United States Patent
Kudo et al.

(10) Patent No.: US 10,289,641 B2
(45) Date of Patent: May 14, 2019

(54) CLUSTER MAPPING BASED ON MEASURED NEURAL ACTIVITY AND PHYSIOLOGICAL DATA

(71) Applicant: Accenture Global Services Limited, Dublin (IE)

(72) Inventors: Takuya Kudo, Santiago del Estero (JP); Atsushi Onda, Setagaya-ku (JP); Ryosuke Nakahata, Meguro-ku (JP); Kaori Shimatsu, Yokohama (JP); Mayumi Kimoto, Shinjuku-ku (JP)

(73) Assignee: Accenture Global Services Limited, Dublin (IE)

( * ) Notice: Subject to any disclaimer, the term of this patent is extended or adjusted under 35 U.S.C. 154(b) by 658 days.

(21) Appl. No.: 14/885,833

(22) Filed: Oct. 16, 2015

(65) Prior Publication Data

US 2017/0109437 A1    Apr. 20, 2017

(51) Int. Cl.
*G06F 16/35*    (2019.01)
*A61B 5/16*    (2006.01)
(Continued)

(52) U.S. Cl.
CPC ............ *G06F 16/35* (2019.01); *A61B 5/165* (2013.01); *G06F 16/334* (2019.01); *G06F 19/00* (2013.01); *A61B 5/0476* (2013.01)

(58) Field of Classification Search
CPC ............................. G06F 16/35; G06F 16/334
See application file for complete search history.

(56) References Cited

U.S. PATENT DOCUMENTS 7,017,110 B1 * 3/2006 Chi .................. G06F 17/30855
707/E17.013
8,732,101 B1 * 5/2014 Wilson .................. G06N 3/063
706/15
(Continued)

FOREIGN PATENT DOCUMENTS

CN    103077490    5/2013

OTHER PUBLICATIONS

"About Mapumental," [online]. 'Mapumental', retrieved on Feb. 9, 2016. Retrieved from the Internet: URL: https://mapumental.com/about, 3 pages.

*Primary Examiner* — Robert W Beausoliel, Jr.
*Assistant Examiner* — Nirav K Khakhar
(74) *Attorney, Agent, or Firm* — Fish & Richardson P.C.

(57) ABSTRACT

Techniques are described for determining recommended tourist based on the real time collection and analysis of biological information regarding users. Sensors in proximity to a user may collect neural activity data (e.g., brain wave data) and physiological data (e.g., blood pressure, heart rate, blood sugar level, etc.). The biological information may be analyzed to determine, for each user, an emotion metric indicating an emotional state of the user at various times. The emotion metrics may be correlated with location data to determine the emotion metric of the user at various sites during a trip. Tag metadata describing the location(s) may be clustered through semantic analysis to generate clusters of semantically similar tags. Emotion metric scores for the clusters may be employed to predict destination(s) where the user(s) may exhibit positive emotion metrics, and the predicted destination(s) may be presented to users in advertisements or other content.

37 Claims, 18 Drawing Sheets

(51) Int. Cl.
    *G06F 16/33*     (2019.01)
    *G06F 19/00*     (2018.01)
    *A61B 5/0476*    (2006.01)

(56) References Cited

U.S. PATENT DOCUMENTS

| | | | |
|---|---|---|---|
| 9,396,199 B1* | 7/2016 | Bartlett | G06F 17/50 |
| 2002/0007393 A1* | 1/2002 | Hamel | G06F 17/30902 |
| | | | 709/203 |
| 2012/0054514 A1* | 3/2012 | Barsness | G06F 1/329 |
| | | | 713/320 |
| 2013/0018954 A1* | 1/2013 | Cheng | G06Q 10/00 |
| | | | 709/204 |
| 2014/0019867 A1* | 1/2014 | Lehtiniemi | G06Q 50/01 |
| | | | 715/738 |
| 2014/0258270 A1 | 9/2014 | Reese et al. | |
| 2015/0067708 A1* | 3/2015 | Jensen | H04N 21/4756 |
| | | | 725/10 |
| 2015/0169780 A1* | 6/2015 | Mishra | G06F 3/011 |
| | | | 707/748 |
| 2016/0055236 A1* | 2/2016 | Frank | G06F 17/30702 |
| | | | 707/748 |
| 2016/0173542 A1* | 6/2016 | Wieczorek | G06Q 10/1093 |
| | | | 715/753 |

\* cited by examiner

Emotion metrics 124

| userID | date | time | emotion evaluating index |
|---|---|---|---|
| 1 | 2015/6/1 | 12:30 | 37 |
| 1 | 2015/6/1 | 12:55 | 60 |
| 2 | 2015/6/1 | 14:30 | 92 |
| 2 | 2015/6/1 | 14:40 | 49 |
| 2 | 2015/6/1 | 16:30 | 88 |

*FIG. 2*

Physiological metrics 126

| userID | date | time | condition |
|---|---|---|---|
| 1 | 2015/6/1 | 12:30 | 1 |
| 1 | 2015/6/1 | 12:55 | 1 |
| 2 | 2015/6/1 | 14:30 | 1 |
| 2 | 2015/6/1 | 14:40 | 0 |
| 2 | 2015/6/1 | 16:30 | 0 |

*FIG. 3*

| ID | Latitude, Longitude | landmark | spot name Lv.1 | spot name Lv.2 | tagged information | business hours |
|---|---|---|---|---|---|---|
| 1 | 48.860586, 2.33767 | Louvre Museum | Mona Lisa | - | Flipnote/Painting | 10:00-18:00 |
| 2 | 48.861080, 2.33587 | Louvre Museum | Pyramide du Louvre | - | Monument | 10:00-18:00 |
| 3 | 48.862026, 2.33585 | Louvre Museum | Le Café Marly | - | Café/Restaurant | 10:00-18:00 |
| 4 | 48.805119, 2.12226 | Palace of Versailles | Royal Chapel | stained glass | Flipnote/Building | 10:00-18:00 |
| 5 | 48.804033, 2.12136 | Palace of Versailles | Le Grand Café d'Orléans | - | Café/Restaurant | 10:00-18:00 |

Location metadata 132

Statistical correlation(s) 1002 (e.g., between combined emotion metrics for users)

Recommendation degrees 1004

| user1 confid 1 | | cluster | | | | | | | | | Correlation with user |
|---|---|---|---|---|---|---|---|---|---|---|---|
| ID | | 1 | 2 | 3 | 4 | 5 | 6 | 7 | 8 | 9 | 10 | |
| Z | 1 | - | 40 | 20 | - | - | - | - | 10 | 10 | 50 | 1.000 |
| A | 1 | 50 | 30 | 40 | - | - | - | - | 10 | 20 | 10 | 0.063 |
| B | 1 | - | - | - | 10 | - | 20 | 40 | 50 | 40 | 0 | -0.982 |
| C | 1 | 20 | 30 | 20 | 10 | - | 40 | 30 | 20 | 10 | 40 | 0.941 |
| D | 1 | 20 | - | - | 20 | 40 | 50 | 10 | 20 | 50 | 50 | 0.500 |
| E | 1 | - | 50 | 0 | - | 50 | 10 | - | 10 | 10 | 20 | 0.615 |
| recommended degree | | 20.00 | 40.00 | 10.00 | 15.00 | | 33.33 | 20.00 | 16.67 | 23.33 | 36.67 | |

Recommended cluster 1006 (e.g., with highest recommendation degree)

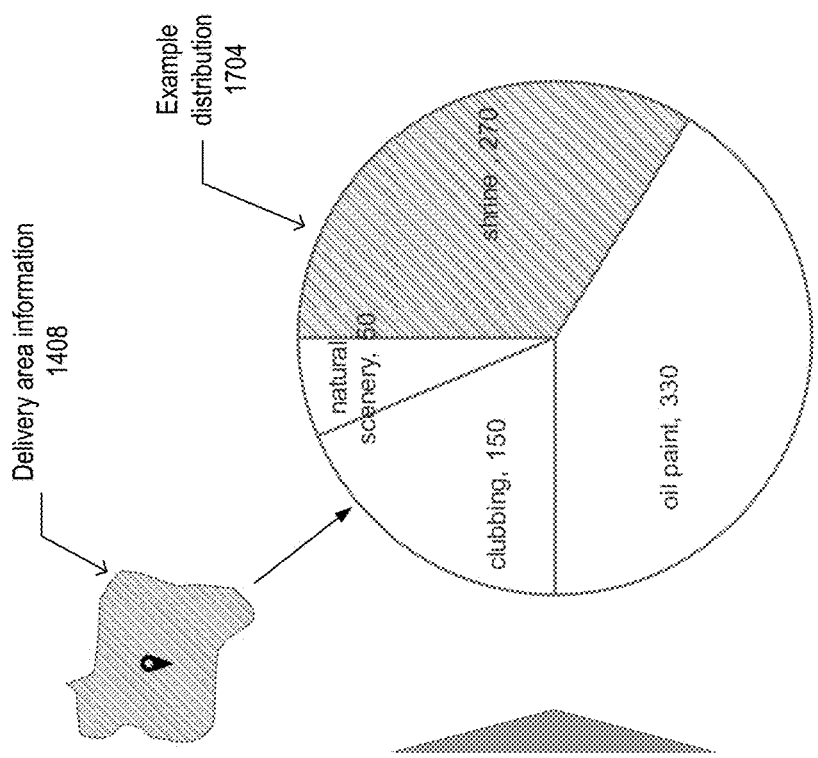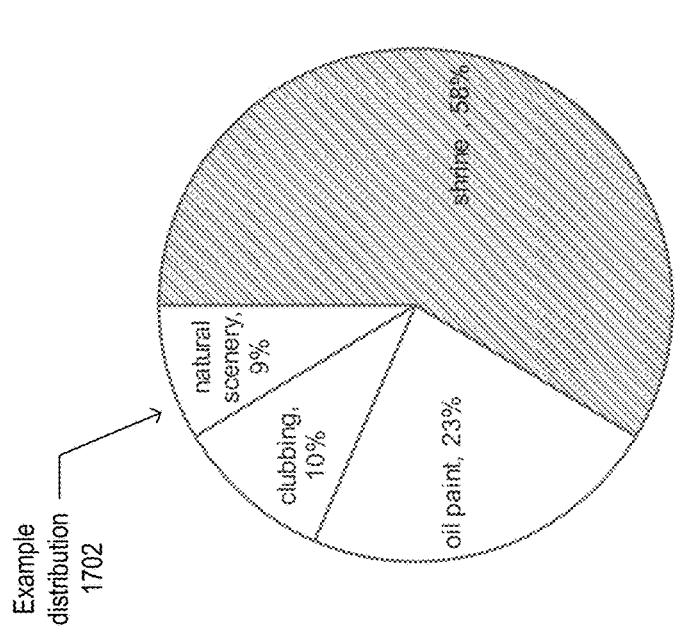
FIG. 17

CLUSTER MAPPING BASED ON MEASURED NEURAL ACTIVITY AND PHYSIOLOGICAL DATA

BACKGROUND

A tourist traveling in an unfamiliar city may read reviews of tourist sites, restaurants, hotels, or other locations to determine whether to visit particular locations. Such reviews may be published on review sites, online travel guides, blogs, or elsewhere. Because traditional reviews are manually written by reviewers, such reviews may be based on the subjective recollections of reviewers and may even be biased. In some cases, the editors of a site may review or attempt to verify the factual accuracy of at least some of the reviews published on the site. However, apart from the word of the author, editors currently have no way to independently and objectively verify that the author of a review actually had the positive (or negative) experience while visiting a location as described in the review.

Moreover, travel guide services or reviews currently used by tourists may not necessarily provide individually relevant information due to mismatches between the interests and preferences of tourists and reviewers. Rating systems and reviews may paint a distorted picture of a location or service if a small number of tourists do most of the voting. Moreover, recollections and emotions about travel destinations may change with the passage of time and based on opinions of others or fading recollections. Accordingly, reviews written after the trip may fail to correctly reflect the emotions experienced by the reviewer during the trip. Further, although tourists may have different goals for a trip and may be excited by different aspects of the destination, the reviews posted on review sites may generalize the evaluation of tourist destinations and may lack specific evaluations of particular sites. Thus, tourists may miss potentially interesting sites and instead visit the more commonly visited and more frequently reviewed locations.

SUMMARY

Implementations of the present disclosure include computer-implemented methods for cluster mapping of location metadata based on neural activity data (e.g., brain wave data) and physiological data collected from users. Implementations may employ clusters of semantically similar location metadata, as well as measured neural activity data and/or physiological data of users, to provide information to tourists or other users regarding locations to visit or businesses to patronize. Implementations may also provide information to advertising platforms, tour companies, or other third parties to enable such parties to provide the recommended destination information to tourists, or otherwise promote products and services to tourists or other individuals. In some implementations, actions of computer-implemented methods include: analyzing neural activity data to determine an emotion metric indicating an emotional state of the user at one or more times, the neural activity data generated through measurement of neural activity of the user at the one or more times; correlating the emotion metric at the one or more times with location data indicating one or more locations of the user at the one or more times, the correlating to determine the emotion metric for the user corresponding to each of the one or more locations; based on location metadata including descriptive tags for locations, determining clusters of locations based on a degree of semantic similarity between the descriptive tags; determining a combined emotion metric for each of the clusters, based on the emotion metric corresponding to the one or more locations with descriptive tags included in the respective cluster; based at least partly on the combined emotion metric, determining the at least one recommended destination for the user; and communicating recommendation information for presentation on a computing device, the recommendation information describing the at least one recommended destination.

In some implementations, the neural activity data includes a plurality of neural oscillation types exhibited by the user; and analyzing the neural activity data to determine the emotion metric further includes: analyzing the plurality of neural oscillation types to determine a plurality of secondary emotion metrics at each of the one or more times; and determining the emotion metric based on the plurality of secondary emotion metrics. The plurality of secondary emotion metrics may indicate one or more of: a level of favor of the user; a level of interest of the user; a level of attention of the user; or a level of stress of the user.

In some implementations, the neural activity data is measured by at least one neural activity sensor in proximity to the user.

In some implementations, determining the at least one recommended destination further includes: identifying a cluster for which the combined emotion metric is an extremum among the clusters; and determining the at least one recommended destination for which a corresponding location tag is in the cluster.

In some implementations, determining the at least one recommended destination further includes: determining the at least one recommended destination having a location that is within a threshold distance of a current location of the user.

At least some implementations may include: analyzing physiological data to determine at least one physiological metric of the user at one or more times, the physiological data generated through measurement of one or more physiological variables of the user at the one or more times; and correlating the at least one physiological metric at one or more times with the location data to determine the at least one physiological metric for the user at each of the one or more locations; wherein determining the at least one recommended destination for the user is further based, at least in part, on the at least one physiological metric for the user. The one or more physiological variables may include one or more of: blood pressure; heart rate; or blood sugar level. In some implementations, the physiological data is measured by at least one physiological sensor in proximity to the user. In some implementations, the at least one physiological metric includes one or more of: a hunger level of the user; or a fatigue level of the user.

In some implementations, determining the at least one recommended destination for the user further includes: accessing other combined emotion metrics for each of the clusters, the other combined emotion metrics determined based on emotion metrics for other users exhibiting physiological metrics corresponding to a physiological metric of the user; determining a statistical correlation between the combined emotion metrics of the user and the other combined emotion metrics of other users; determining a recommended cluster for which an average of one or more of the other combined emotion metrics of the other users is an extremum; and determining the at least one recommended destination for which a corresponding location tag is in the recommended cluster. In some implementations, the average of the one or more of the other combined emotion metrics is weighted based on the statistical correlation. At least some implementations may include determining the one or more of the other combined emotion metrics for which the statistical correlation exceeds a threshold.

In some implementations, the recommendation information includes at least one advertisement for the at least one recommended destination.

Other implementations include corresponding systems, apparatus, and computer programs, configured to perform the actions of the methods, encoded on computer storage devices.

Implementations of the present disclosure provide one or more of the following advantages. Recommendations may be generated for a user based on real time, up to date information regarding the user's biological state (e.g., brain wave activity, blood pressure, blood sugar level, heart rate, etc.), providing recommendations that are more relevant to the particular user, and that are more current, unbiased, and objective compared to traditional reviews. Moreover, through the use of high-precision location information, recommendations may be tuned to more specific locations compared to traditional reviews, such as a particular painting with a museum. By determining recommended destinations based on the analysis of real time information regarding the user's biological state, by developing emotion metric(s) for users based on the real time biological state information, and through the semantic (e.g., natural language-based) clustering of tag metadata, implementations improve the functioning of computing devices configured to generate tourist information, advertising campaigns, marketing campaigns, or other travel-related content.

In some implementations, a location may be associated with various metadata such as a facility or location name (e.g., Griffith Observatory, Louvre Museum, etc.), location coordinates (e.g., latitude and longitude) of the location or of particular highlight(s) within the location (e.g., "Mona Lisa" and "Venus de Milo" in the Louvre Museum), and tag data describing the locations or the highlights within the locations, such as "Mona Lisa" tagged as "western oil painting," "Venus de Milo" tagged as "western sculpture", and so forth.

In some cases, one or more tour businesses may register the target audience's nationality, age, spoken language, or other demographic characteristics. The tour business(es) may also specify a broadcast range, time period, or other aspects of a promotional campaign to promote locations and sites to current tourists, future tourists, or potential tourists. Location data for the tourists may be collected, based on signals from satellite navigation services (e.g., Global Positioning System) or other data. In some cases, the location data may be high-precision, accurate within one or two meters. Neural activity data (e.g., brain wave data) and/or physiological data (e.g., heart rate, blood pressure, blood sugar level, etc.) may be collected from one or more users at one or more locations.

Tag data associated with one or more potential destinations, such as locations or highlighted sites within locations, may be clustered through semantic processing. The location coordinates of potential destinations and/or highlight sites, the location data, neural activity data, and physiological data of users, and the cluster data may be analyzed (e.g., organized and collaboratively filtered) to determine clusters exhibiting similar emotion metrics across various users.

Recommended destinations may be determined based on the determined similar clusters. Recommended destinations may include any number of locations, or particular highlight sites within locations, that are estimated to induce positive emotions in users. Recommended destinations may be sent to users and presented in a user interface of an application executing on a mobile device or other computing device. Additional content may also be presented to users, such as advertisements determined based on the analysis. The advertisements may advertise particular businesses or other locations (e.g., restaurants, stores, tourist attractions, etc.), and may be selected and presented to those users who are likely to experience a positive emotional response at the advertised location, as determined through the analysis described herein.

In addition, implementations also provide for advertising platform(s), marketing platform(s), or other services that are configured to match emotional compatibility between the destinations and tourists. Such platform(s) or service(s) may be provided for use by tour businesses, restaurants, retailers, or other commercial entities. Revenue for the entities may be increased by utilizing high-precision location data, selecting locations with high numbers of tourists, and sending out push notifications or other communications to promote destinations to users who are determined as likely to have a positive experience at the destinations. Implementations enable advertising campaigns with high conversion rate (CVR) (e.g., resulting sales) achieved through the analysis of emotion metrics, location of tourists during a trip, selection of target audience, and improvement of targeting precision. For example, data may be collected regarding a particular Canadian tourist in their 20 s who had exhibited excitement while visiting Avalon, a bar/night club in Hollywood. The particular tourist, or demographically similar tourist(s), may be presented with information describing a lively café with a high number of young patrons in a socially vibrant scene, instead of information on a quieter restaurant serving no alcohol. Moreover, future advertisement campaign guidelines and menus may be developed or refined based on the understanding of the interplay between demographic characteristics and the emotion metrics of tourists objectively determined based on neural activity data and/or physiological data as described herein.

Implementations provide various advantages over traditional travel guide services and review sites. Destination recommendations may be determined without regard to the potentially biased mass posting of tourists, spam postings, or other potentially unreliable data. Neural activity data, physiological data, and location data may be collected from tourists or other users and analyzed to determine recommended destinations, and may be collected even from tourists or other users who may not otherwise write reviews in the traditional manner. Accordingly, implementations provide for destination recommendation based on a broader set of input data than may be employed by traditional reviews or travel guides. Moreover, because the input data (e.g., neural activity data and/or physiological data) is collected at the time when the user(s) are at or near the locations being evaluated, implementations avoid the problem of reviews becoming less accurate over time due to the forgetfulness of reviewers or later-introduced biases. Finally, implementations provide for the quantitative evaluation of individual highlight sites (e.g., "Mona Lisa") within larger locations (e.g., Louvre Museum), as well as quantitative evaluation of the larger locations, and may provide recommendations of rarely visited or less commonly visited destinations that is provided by traditional review sites or travel guides.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF DRAWINGS

FIG. 2 depicts an example of emotion metrics that may be employed in implementations of the present disclosure.

FIG. 3 depicts an example of physiological metrics that may be employed in implementations of the present disclosure.

FIG. 6 depicts an example of location metadata that may be employed in implementations of the present disclosure.

FIG. 10 depicts an example of analyzing combined emotion metrics for multiple users to determine a recommended cluster according to implementations of the present disclosure.

FIG. 17 depicts an example of achieving an optimal conversion rate for advertising a site, according to implementations of the present disclosure.

DETAILED DESCRIPTION

Figure 1:
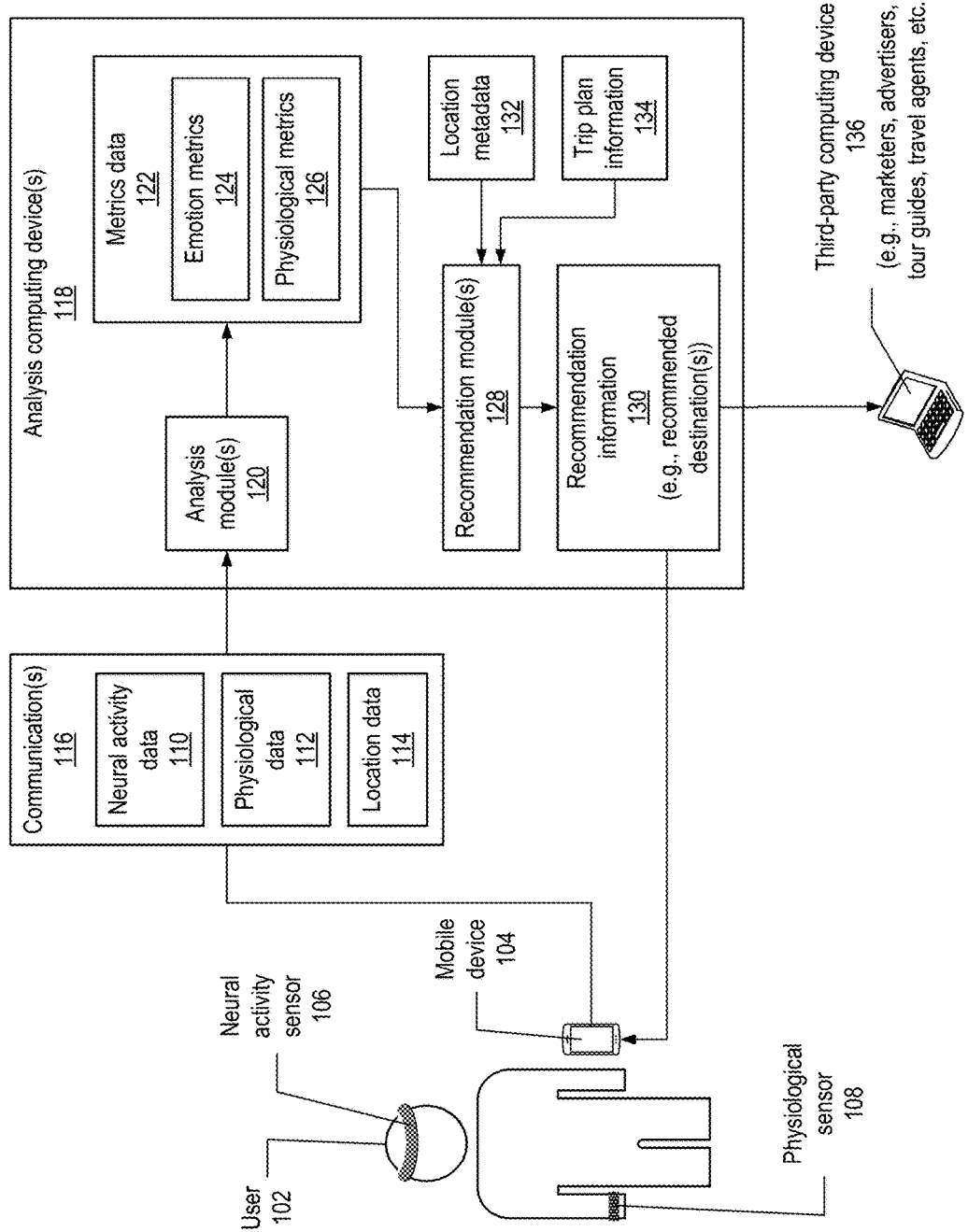
FIG. 1 depicts an example system that can execute implementations of the present disclosure.

Implementations of the present disclosure are directed to systems, methods, devices, and computer-readable media for determining recommended destinations (e.g., travel destinations) for a tourist or other user based on the analysis and correlation of real-time neural activity data (e.g., brain wave measurements), physiological data (e.g., blood pressure, heart rate, blood sugar level), and location information. Such data may be analyzed to determine locations where a particular user previously had negative or positive experiences. Based on a semantic analysis of metadata describing locations, implementations may identify one or more recommended destinations where the user is likely to have a positive experience, based on a semantic similarity between metadata describing the recommended destinations and metadata describing other locations where the user (or similar users) had positive experiences.

Neural activity data may be measured by a sensor that is worn by the user. Physiological data may be measured by the same sensor, or a different sensor, worn by the user. For example, the user may wear a FitBit™ or similar device that measures physiological variables such as heart rate, blood pressure, blood sugar level, and so forth. This data may be analyzed to determine the sites where the user was excited or happy, based on a combination of high precision (e.g., within a meter) location information, brain wave measurements, blood sugar levels, and so forth. The sites may be analyzed to identify their common aspects, such as sites where the user was able to view paintings, eat pastries, race cars, and so forth. Further destinations may be recommended based on the analysis. In this manner, implementations may improve on the arbitrariness or bias present in traditional reviews by providing a more objective, data-based technique for recommending destinations for a user.

Implementations may also suggest a route for a user that takes into account the user's hunger or fatigue state. By determining the hunger or fatigue that the user is currently experiencing, or about to experience, based on measured blood sugar levels or other variables, implementations may provide a recommended destination at a time when the user may be in need of rest, food, or drink. By acquiring neural activity data and physiological data in real time, implementations may provide an alert to a user in the form of recommended destination information that is timed according to the user's current biological state. Moreover, in some implementations information regarding sites that were of interest to the user, or to similar users, may be provided to travel agents, tour operators, marketing professionals, or others, and employed to identify content, destination, travel packages, or other information suited for the user.

Implementations may also employ highly accurate, location-specific information about sites to make more granular recommendations than is possible using traditional reviews. For example, the user's biological information (e.g., neural activity data and/or physiological data) may indicate that the user enjoys paintings but is bored by sculptures, based on the correlation of the biological information with fine-grained location information describing the particular positions of sculptures and paintings in a museum. Such data may then be employed to recommend destinations where the user may view paintings instead of sculpture.

In some implementations, various types of entities may be the recipients of information produced through the analysis of neural activity data, physiological data, and location data described herein. Such entities may include tourists seeking information regarding tourist destinations on a personalized level, and business entities (e.g., tour businesses, marketers, or advertisers) seeking to increase revenue by providing advertisements or other content with a higher CVR compared to traditionally determined advertisements or other content sent to tourists. To determine the optimally personalized information on tourist destinations for the tourists and to allow the tour businesses to execute an effective advertising campaign, the tour businesses may provide information including, but not limited to: a name of each tourist destination; information on the highlight sites within each tourist destination; location data (e.g., latitude and longitude) of the destination and/or the highlights; or the tag data used for classification of the genres of the highlights, or other descriptive information. In some cases, registration of the tag data may include one tag per highlight site.

A management application (e.g., designed for tour businesses) may be downloaded by one or more tour businesses. After starting up the application, the various information regarding the destinations may be registered using the application. For example, the names of tourist destinations may be entered in full (e.g., Griffith Observatory, Louvre Museum, etc.). Information describing the individual highlight sites within the tourist destination(s) may also be registered (e.g., "Mona Lisa" and "Venus de Milo" displayed in Louvre Museum). The system may detect tourist(s) who visit the actual exhibition and register the latitude and longitude data of the highlights with a user application. Tag data may added to the registration to allow classification of the highlights by genres. (e.g., "western oil painting" for "Mona Lisa", "western sculpture" for "Venus de Milo", etc.). The registered data may be sent to a server that manages data for particular region(s) or data for all regions.

Tour businesses may register their advertising campaigns to increase revenue and number of customers. Implementations may provide an advertising platform that includes various advantages over traditional advertising platforms. For example, a broadcast range may be determined by reverse engineering the estimated travel time of the travelers to reach the tourist destination. In some cases, the calculation of the possible movement range from a reference point within a certain amount of time may be determined using the Mapumental tool released by mySociety. Using the emotion metrics data generated by implementations, a tour business may refine the target audience of its advertising campaign to include tourists who are determined to be emotionally compatible for the recommended destinations (e.g., tourists who may have a positive emotional experience when visiting the recommended destinations). This may be achieved through an analysis report provided to the tour business, the report including information on travelers within a recent time period (e.g., the last month) such as the proportion of tourists showing a positive emotional response. The report may describe a number or proportion of tourists showing a positive emotional response while visiting a "western oil painting" such as the Mona Lisa, tourists showing positive emotional response while visiting Avalon, a "night club," and tourists showing positive emotional response while visiting a "western sculpture" such as the Venus de Milo. The emotion metrics may differ from tourist to tourist during a visit to the tourist destinations. An advertising campaign with higher CVR may be realized through selective broadcast of the advertisement to tourists who are compatible with the various destinations and whose location and trip itinerary allow them to reach the tourist destinations.

Advertising campaigns may be managed through a management application designed for the tour businesses and presentable via a web application or native application. Tour businesses signing up for an advertisement campaign may also be provided with reports describing the nationality, gender, age, or other demographic characteristics of tourists, as well as data indicating a trend of destinations showing positive emotion metrics associated with the tourist destinations operated by the tour businesses (e.g., a higher positive emotional response towards a western oil painting, a statue of Buddha, etc.). Based on the report, the tour business can select the intended target audience's nationality, gender, age, or other demographic characteristics. The tour business may select the broadcast region determined with a reference point selected by the tour business. The reference point may be based upon the following: the range based upon the radius distance from the reference point, e.g., in increments of 500 m, 1 km, 2 km, 3 km, etc.; and the range based upon a reasonable travel time between the locations, by foot travel or transit, e.g., in increments of 30 min, 1 hour, 2 hours, etc. or by period 1 day, 3 days, 1 week as determined by the tour businesses. A tour business may also preregister the campaign contents, such as public relations materials regarding tourist destinations, discount coupons for admission, and so forth. Based upon the registered conditions, the advertisement campaign may be shown to any number of tourists. In some cases, the campaign may be shown to the maximum possible number of people. Among the tourists who are shown the campaign, trends of positive emotional response among tourists visiting their tourist destinations (e.g., within the last month) may be analyzed, and the advertisements may be subsequently broadcast towards a refined tourist pool with compatible interests compared to the destinations. In this way, an advertisement campaign with high CVR may be realized.

To realize both a better tourist destination information supply for the tourists and an advertisement campaign with high CVR for the tour businesses, various data may be acquired from the traveling tourists. The first piece of data may include high-precision location data (e.g., with the deviation within 1-2 m), showing the movement route of the tourists. The second piece of data may include the tourist destinations and trip plan information scheduled by the tourists. The third piece of data may include neural activity data or physiological data such as the heart rate of the tourists. The high-precision location data can be utilized to associate the detailed information on the highlights within the tourist destinations and the emotion metrics. The second piece of data, the trip plan information, may be utilized to display the recommended destination information on the application for the tourists, as well as to remove tourist destinations deemed too difficult to be visited during the trip's idle time from the recommendations, and thus improving the accuracy of the advertising campaign. The third piece of data may be utilized to determine the emotion metrics of the tourists.

Acquisition methods for each type of data are explained further below. The first piece of data, the high-precision location data, may be measured in real time (e.g., every 10 seconds) via the GPS data retrieved from the mobile devices and sent to data storage. The data storage including the high-precision location data may include an identifier (ID) of a tourist (e.g., a specific ID may be assigned to each tourist), latitude and longitude data of the tourist, and the time stamp of the data retrieval.

The second piece of data, the trip plan information, may be registered by the tourist at any point of time, by starting up the application and entering any number of destinations or estimated visit times. The destination may be displayed in the form of pull-down menu, based upon the tourist destinations entered by the tourists. The trip registration process can be completed by selecting the matching result from the displayed items and clicking the "Register" button. Through this registration of the trip, tourist destinations deemed to be difficult for visit during the idle time of the trip may be eliminated from the recommendation, and thus improving the accuracy of the advertisement campaign.

The third piece of data, e.g., physiological data and neural activity data, may be measured by wearable devices such as the Fitbit and Apple Watch. Data retrieved from the wearable devices capable of measuring the heart rate may be sent to smartphones registered with the tourist-use applications via Bluetooth. Afterwards, the heart rate data may be transferred to the data storage via the application on the mobile device. The table sections of the data storage may include the ID of the tourist, heart rate or other physiological or neural activity data, and the time stamp of data retrieval. For example, based upon the heart rate data retrieved, locations where the tourists experience higher heart rate than usual (e.g., locations at which tourists experience 30% or higher heart rate than usual value within 1 minute) may be classified as positive emotional response along a scale from 0-100, through correlation with the high-precision location data, so as to determine the positive emotional response of each tourist within the tourist destinations and to store it as data. In some cases, the high-precision location data, the heart rate data (or other physiological and/or neural activity data), and the derived emotion metrics data are stored in the data storage and utilized during the creation of recommendations.

The tag data registered for each highlight within the tour facility or destination may be processed semantically and clustered. In some cases, the tags data registered by the tour businesses may be disassembled with generic morphological analysis method. For example, "western sculpture" may be broken down into two terms, western and sculpture. This can be analyzed through various morphological analysis methods. In some implementations, during the analysis phase, an open source morphological analysis engine such as MeCab may be utilized. After disassembling the terms, a repetition frequency of each element may be tallied, and extremum at the lower end of the repetition frequency may be considered as statistical noise and removed from future clustering. After the elimination process, the correlation between each element may be calculated, and by implementing the correlation factor between the elements as the explanatory variable within the tag clustering, tags with display-name variation and similar signification may be grouped into clusters. The most optimal group number of the clustering result may be determined with generally adopted statistical standards such as the CCC, pseudo-F value, and pseudo-t value.

The latitude and longitude data corresponding to each location, the tourist's location, physiological data, and neural activity data, and the cluster data may be collaboratively filtered and clusters with similar emotion metrics may be determined. A collaborative filtering method may be adopted to quantify the recommendation of the tag groups for tourists without actual emotion metrics. With the collaborative filtering method, the emotion metrics of the tourists and of the tag groups may be determined.

Correlation between the tourists are analyzed with the emotion metrics, and recommendations may be made based upon the assumption that similar tourists tend to be positively excited by similar destinations. The analysis process may include the following steps. A correlation factor between the tourists may be calculated based upon the emotion metrics of each tag group. The result may be filtered down to tourists with high correlation factor. The filtered tourists may be compared against the emotion metrics of other tag group(s), by superimposing the correlation factor calculated in the first step, and the weighted average value may be calculated. For example, per the examples in FIGS. 8-11, to determine whether the tag group 5 is recommended for Tourist Z or not, the correlation factor between Tourist Z and Tourist A may be RZA, and a determination may be made that RZA=0.063. In some cases, the correlation factor is calculated by utilizing the actual tag group data in both tourist groups. The correlation factors may also be calculated for Tourists B-E. The higher the derived correlation factor, the closer the interests of the tourists resemble each other, and the likelier that the tourist may experience positive emotional response when exposed to similar tag group. Therefore, tourists with correlation factor higher than 0.4 may be defined as highly similar customers. By utilizing the emotion metrics superimposed with the correlation factor, a recommendation factor (e.g., recommendation degree 1004) SZ5 of the Tag Group 5 for Tourist Z can be calculated as SZ5=(SD5×RD5+SE5×RE5)÷(RD5+RE5)=(40×0.500+50× 0.615)÷(0.500+0.615)=45.5. In the example of FIG. 10, due to a lack of actual result in Tag Group 5 for Tourist C, Tourist C may be removed from the calculation.

The optimal tourist destinations, e.g., those determined to induce positive emotional response in the event of an actual visit, may be selected from among the tourist destinations in the tag data clusters. By utilizing the trip plan registered by the tourist, destinations too far or too difficult to be visited on the current trip may be identified and omitted from the recommended destination(s). In some cases, if a long travel distance separates the current location of a tourist from a possible destination, the destination may be omitted. For example, a destination may be omitted if it is at a distance requiring 5 hours or longer of one-way journey. A destination may also be omitted if visiting the destination would impact the trip, e.g., such as a location requiring more than 3 hours of one-way journey when there is less than 3 hours until the next scheduled destination on the itinerary. In some cases, previously visited tourist destinations, determined by referring to a tourist history in the application, may also be omitted. The final set of recommended tourist destinations may be presented in the application on a mobile device or other computing device of the tourist. Presented content may also include the advertisements registered by the tour businesses as described above.

FIG. 1 depicts an example system that can execute implementations of the present disclosure. As shown in the example of FIG. 1, a user 102 may carry, wear, or otherwise convey a mobile device 104 such as a smartphone, tablet computer, notebook computer, laptop computer, wearable computer, implanted computer, electronic book reader, automotive computer, and so forth. The user 102 may wear, carry, or otherwise be in proximity to a neural activity sensor 106 and a physiological sensor 108. In some implementations, neural activity data 110 (e.g., brain wave activity, neural oscillation activity) is measured by the neural activity sensor 106. Physiological data 112 may also be measured by the physiological sensor 108. The neural activity data 110 and the physiological data 112 may be measured by different sensors, or by a same set of one or more sensors. In some cases, the neural activity sensor 106 is worn on the user's head. In some cases, the physiological sensor 108 is configured to be worn on the user's wrist, such as a FitBit™. Physiological data 112 may include, but is not limited to, measurements of the user's blood pressure, heart rate, or blood sugar level. Measurements of physiological data 112 and neural activity data 110 may be taken at one or more times. The physiological data 112 and the neural activity data 110 may be measured at the same time(s) or at different time(s). The physiological data 112 and neural activity data 110 may be received by the mobile device 104 via a Bluetooth connection, a near field communication (NFC) connection, or other type of signal sent from the sensor(s) to the mobile device 104.

The mobile device 104 may send the neural activity data 110 and the physiological data 112 in one or more communications 116 to one or more analysis computing devices 118. The mobile device 104 may also generate and send location data 114 describing a location of the mobile device 104, or the user 102, at one or more times. Location data 114 may be generated based on signals received from a satellite-based navigation systems such as the Global Positioning System (GPS), or through other methods. The location data 114 may also be communicated to the analysis computing device(s) 118 in the communication(s) 116. In some implementations, the location data 114 is highly accurate location data that provides locations of the mobile device 104 to within a meter. The mobile device 104 may communicate with the analysis computing device(s) 118 via one or more networks (not shown). Such network(s) may include public networks (e.g., the internet) or private networks. Network(s) may include one or more local area networks (LANs), wide area networks (WANs), wireless LANs (WLANs), or wireless WANs (WWANs). Network(s) may include wireless data networks such as 3G, 4G, Edge, LTE, and so forth. In some cases, the communication(s) 116 are encrypted to prevent unauthorized use of the communicated information. The communication(s) 116 may be secured using a version of transport layer security (TLS) or other protocols. The analysis computing device(s) 118 may include any number and type of computing device, including server computers, network computers, distributed computing systems (e.g., cloud servers), blade servers, and so forth.

The analysis computing device(s) 118 may execute one or more analysis modules 120. The analysis module(s) 120 may analyze the information received in the communication(s) 116 to generate metrics data 122. The metrics data 122 may include emotion metrics 124 and physiological metrics 126. The analysis module(s) 120 may analyze the neural activity data 110 to generate an emotion metric 124 indicating an emotional state of the user 102 at the one or more times when the neural activity data 110 was collected. For example, the emotion metric 124 may indicate one or more of an attention level, a stress level, an interest level, or a favor level of the user 102 at various times. In some implementations, the analysis module(s) 120 may analyze the neural activity data 110 to generate a plurality of secondary emotion metrics indicating the user's level of attention, stress, interest, favor (e.g., happiness), or other emotional states. The analysis module(s) 120 may then combine or otherwise employ the secondary emotion metrics to determine the (e.g., overall) emotion metric 124 of the user 102 at one or more times.

The analysis computing device(s) 118 may analyze the physiological data 112 to generate one or more physiological metrics 126 indicating a physiological state of the user 102 at the one or more times when the physiological data 112 was collected. For example, one or more of the heart rate, blood pressure, or blood sugar level measurements may be analyzed to determine a level of hunger or a level of fatigue exhibited by the user 102 at various times. In some implementations, multiple physiological metrics 126 are generated to indicate particular physiological states of the user 102 with respect to hunger, fatigue, or other states. In some implementations, the physiological metric(s) 126 are binary values indicating whether or not the user 102 is hungry, whether or not the user is fatigued, and so forth.

The metrics data 122, including the emotion metrics 124 and the physiological metrics 126, may be accessed by one or more recommendation modules 128 executing on the analysis computing device(s) 118. The emotion metrics 124 and the physiological metrics 126 may be correlated with the location data 114 to determine, for the user 102, an emotion metric 124 and physiological metric(s) 126 for the user 102 at one or more locations. In some implementations, the recommendation module(s) 128 may also access location metadata 132. The location metadata 132 may include, for one or more sets of location coordinates, a name and description of the location to any degree of specificity. The recommendation module(s) 128 may employ one or more of the emotion metrics 124, the physiological metrics 126, the location data 114, or the location metadata 132 to determine recommendation information 130. The recommendation information 130 may describe one or more recommended destinations for the user 102. In some implementations, the recommendation module(s) 128 may also employ trip plan information 134 to generate the recommendation information 130. The trip plan information 134 may describe the user's itinerary travel plans, lodging arrangements, or other aspects of one or more legs or segments of a trip. Generation of recommendation information 130 is described further with reference to FIGS. 2-12.

The recommendation information 130 may be communicated to the mobile device 104, or another computing device operated by the user 102, and presented to the user 102 via a display, audio output components, or other components of the device(s). In some cases, the recommendation information 130 is sent to third-party computing device(s) 136 associated with third parties such as marketers, advertisers, tour guides, travel agents, and so forth. The recommendation information 130 may enable such parties to determine content, advertisements, products, tour destinations, travel packages, tours, transportation options, lodging, or other information that is relevant to the particular itinerary, emotional state, or physiological state of the user 102.

FIG. 2 depicts an example of emotion metrics 124 for one or more users 102. In some implementations, an emotion metric 124 may be a value along an index (e.g., from 0 to 100), where the value indicates an emotional state of a user 102. In some cases, a lower emotion metric 124 indicates a more negative emotional state (e.g., unhappy, unattentive, stressed, or disinterested) at the time when the neural activity data 110 was measured. A higher emotion metric 124 may indicate a more positive emotional state (e.g., happy, attentive, relaxed, or interested). The emotion metrics 124 may be generated and stored in a table that includes columns indicating the user 102 (e.g., UserID) and the date and time corresponding to the emotion metric 124.

FIG. 3 depicts an example of physiological metrics 126 for one or more users 102. In some implementations, a physiological metric 126 may be a value indicating a condition of the user 102 at the corresponding time. In some implementations, multiple physiological metrics 126 may be calculated. For example, a physiological metric 126 may be determined to indicate a hunger condition of the user 102, e.g., whether the user 102 is hungry or not. A physiological metric 126 may be determined to indicate a fatigue condition of the user 102, e.g., whether the user 102 is fatigued or not. The physiological metric(s) 126 may be binary values indicating whether the user 102 is hungry or not hungry, fatigued or not fatigued, at the time when the physiological data 112 was measured. The physiological metrics 126 may be generated and stored in a table that includes columns indicating the user 102 (e.g., UserID) and the date and time corresponding to the physiological metric 126.

Figure 4:
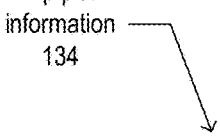
FIG. 4 depicts an example of trip plan information that may be employed in implementations of the present disclosure.

FIG. 4 depicts an example of the trip plan information 134. As shown in the example of FIG. 4, the trip plan information 134 may indicate the date, time, and coordinates for the departure location and destination location of the user 102, corresponding to one or more legs or segments of the user's trip. In some cases, the trip plan information 134 is provided by the user 102 prior to or during the user's travel. The trip plan information 134 may also be determined based on plane ticket information, tour package information, and so forth.

Figure 5:
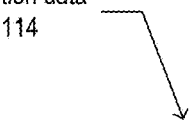
FIG. 5 depicts an example of location data that may be employed in implementations of the present disclosure.

FIG. 5 depicts an example of the location data 114 that may be collected by the mobile device 104 and communicated to the analysis computing device(s) 118. The location data 114 may indicate a location for a user 102 at one or more times (e.g., date and time). The location data 114 may describe location in terms of coordinates, such as longitude and latitude as in the example of FIG. 5. The location data 114 may also describe location using other coordinate systems or via other methods.

FIG. 6 depicts an example of the location metadata 132. As shown in FIG. 6, the location metadata 132 may include any number or records. Each record may include coordinates of a location (e.g., longitude and latitude) and a name of a landmark, site, or point of interest at or near that location (e.g., Louvre Museum). The location metadata 132 may also include, for each location, any number of descriptive tags describing the location in further detail. For example, the descriptive tags may include descriptions of particular spots or sites within the location, such as the Mona Lisa painting in the Louvre Museum. The descriptive tags may also include tagged information describing the location or spots within the location, such as "painting" to describe the Mona Lisa within the Louvre Museum. The location metadata 132 may include records describing a location with varying degrees of specificity. For example, the location metadata 132 may indicate coordinates of the Louvre Museum, coordinates of a particular gallery or cafe within the Louvre, or coordinates of a particular work of art within the particular gallery. The location metadata 132 may provide highly location-specific location information. For example, the location metadata 132 may distinguish between two objects (e.g., two different paintings) that are within one or several meters of one another. The location metadata 132 may also include other information regarding location(s), such as hours of operations. In some cases, tour businesses or other commercial entities, civic organizations (e.g., tourist bureaus), or other third parties may provide location metadata 132 for one or more locations, including metadata describing a larger site (e.g., Louvre Museum) as well as more metadata describing more specific highlight sites within the larger site (e.g., "Mona Lisa" within the Louvre).

Figure 7:
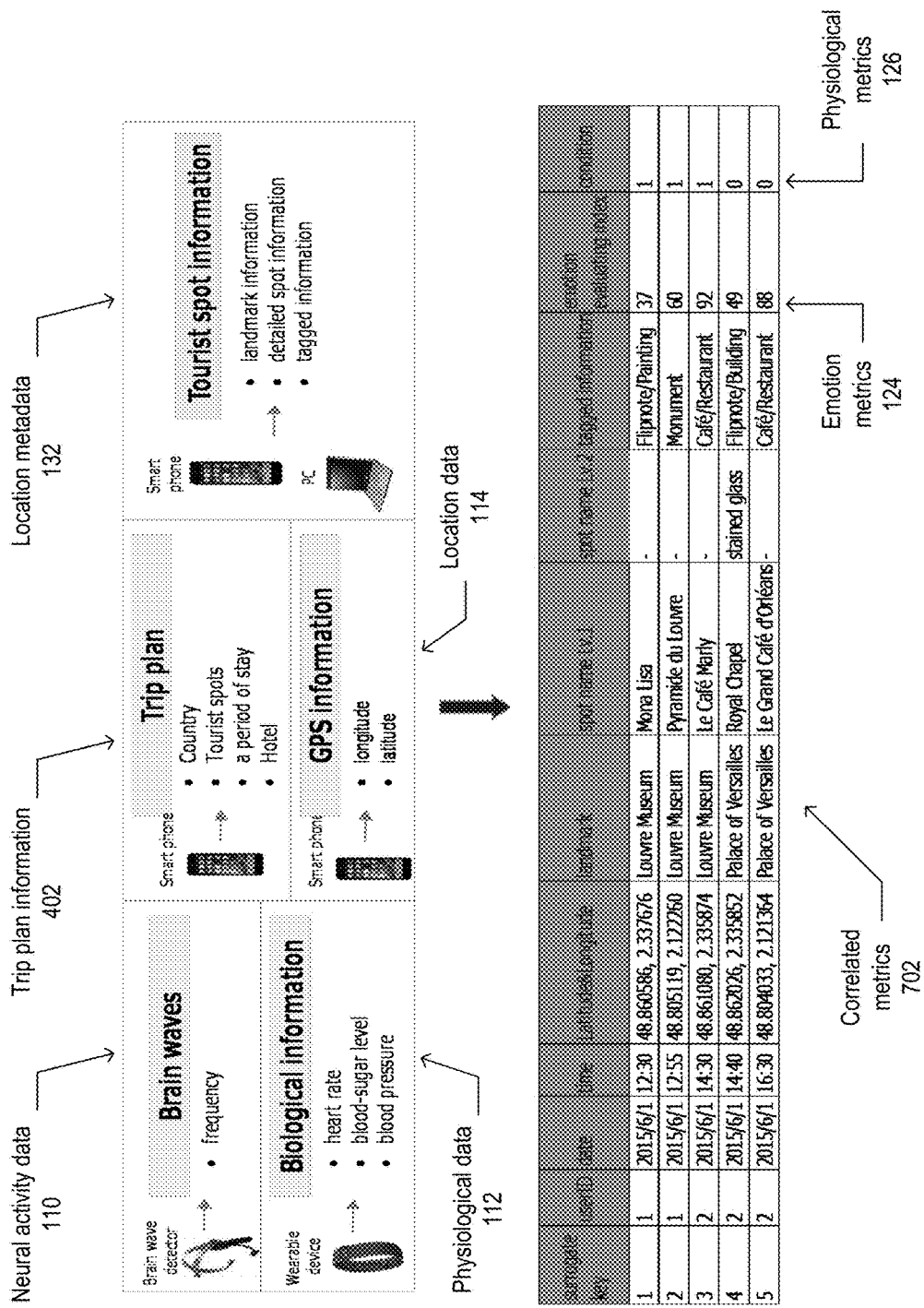
FIG. 7 depicts an example of location-correlated metrics according to implementations of the present disclosure.

FIG. 7 depicts an example of correlated metrics 702 that may be determined by the analysis module(s) 120, the recommendation module(s) 128, or other software module(s), according to implementations of the present disclosure. As shown in FIG. 7, the neural activity data 110 (e.g., brain wave activity), physiological data 112 (e.g., heart rate, blood sugar level, blood pressure), trip plan information 134, location data 114, and location metadata 132 may be correlated or otherwise combined to generate correlated metrics 702. The correlated metrics 702 may include, for a user 102, the emotion metric 124 and one or more physiological metrics 126 associated with one or more locations. The correlated metrics 702 may also include the descriptive tag(s) associated with each location, as indicated in the location metadata 132.

Figure 8:
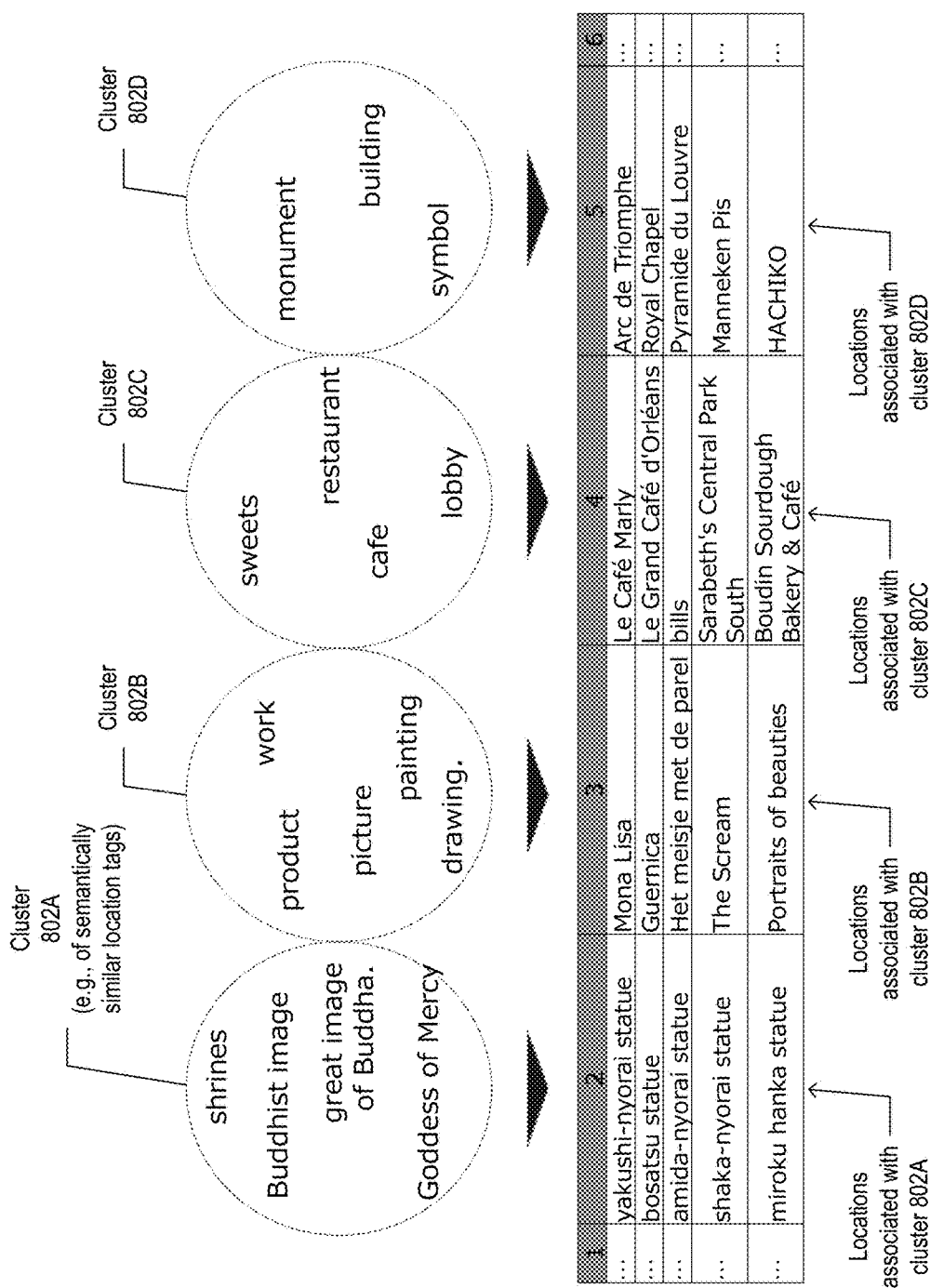
FIG. 8 depicts an example of clusters of locations according to implementations of the present disclosure.

FIG. 8 depicts an example of clusters 802 of locations according to implementations of the present disclosure. In some implementations, the location metadata 132 may be analyzed to determine one or more clusters 802 that includes locations for which the descriptive tags are semantically similar. Semantic similarity may be determined based on a natural language (NL) analysis of the descriptive tags, or through other methods. In some implementations, one or more locations are identified as associated with each cluster 802. Such identification may be based on a semantic similarity between a name of the location and the metadata for the locations in the cluster 802, or a semantic similarity between metadata of the location and the metadata for the other locations in the cluster 802.

Figure 9:
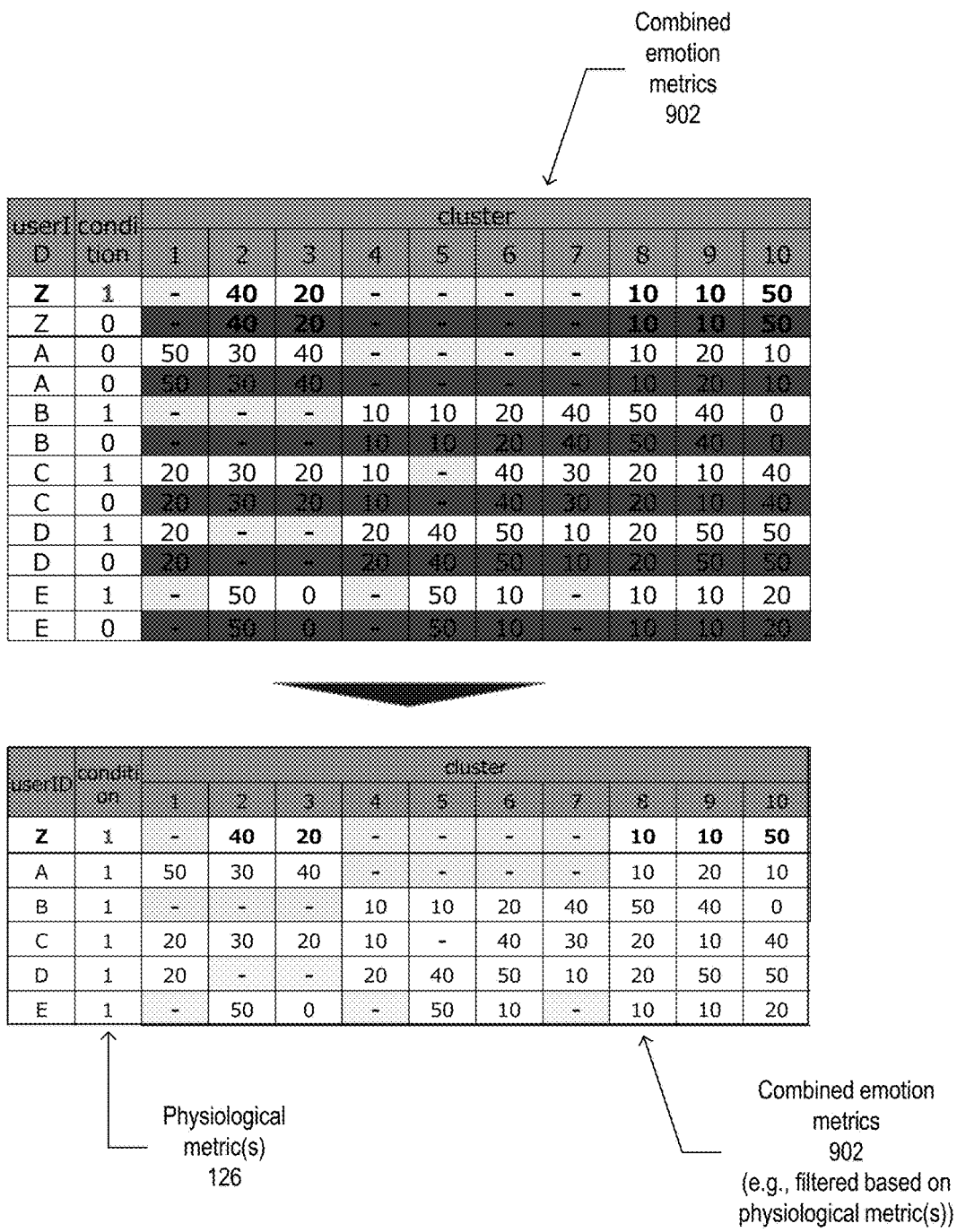
FIG. 9 depicts an example of combined emotion metrics that may be employed by implementations of the present disclosure.

FIG. 9 depicts an example of combined emotion metrics 902 that may be employed by implementations of the present disclosure. In some implementations, a combined emotion metric 902 may be determined for each cluster 802 and for the user 102. The combined emotion metric 902 may be a combination (e.g., sum, average, etc.) of the location-correlated emotion metrics 124 associated with the locations in the cluster 802. FIG. 9 depicts a first table showing an example of combined emotion metrics 902 for a particular user 102 being analyzed (e.g., user Z) and other users 102 (e.g., users A-E). For 10 clusters, the table depicts a combined emotion metric 902 for each cluster 802, for each user 102. FIG. 9 further depicts a second table showing the combined emotion metrics 902 that have been filtered, or otherwise selected, based on physiological metric(s) 126 (e.g., shown as "condition" in FIG. 9). In some implementations, the analysis includes filtering the combined emotion metrics 902 to select those for which the physiological metric 126 of the user 102 being analyzed (e.g., user Z) corresponds to the physiological metrics 126 of the other users 102.

FIG. 10 depicts an example of analyzing the combined emotion metrics 902 for multiple users 102 to determine a recommended cluster 1006 according to implementations of the present disclosure. In some implementations, a statistical correlation 1002 is calculated between the combined emotion metrics 902 of the user 102 being analyzed (e.g., user Z) and those of the other users 102 (e.g., users A-E). For those users 102 exhibiting a statistical correlation 1002 higher than a threshold, implementations may calculate a recommendation degree 1004 for each cluster 802. In some implementations, the recommendation degree 1004 is based on the combined emotion metrics 902 in a cluster 802 for those users 102 exhibiting the higher than threshold statistical correlation 1002.

In the example of FIG. 10, user Z is the user 102 for whom recommendations are being generated, and the combined emotion metrics 902 of other users A-E are being compared to those of user Z for multiple clusters. Three users C, D, and E exhibit a statistical correlation with user Z that is at least the predetermined threshold value of 0.5. For each cluster 802, a recommendation degree 1004 is calculated as an average of the combined emotion metrics 902 of the users C, D, and E for that cluster 802. In some cases, the recommendation degree 1004 is calculated as a weighted average of the combined emotion metrics 902, weighted based on the statistical correlation 1002 for the user(s) 102. Accordingly, the combined emotion metrics 902 of the more highly correlated users may be weighted more heavily in calculating the recommendation degrees 1004. The cluster 802 with the highest recommendation degree 1004 may be designated as a recommended cluster 1006.

Figure 11:
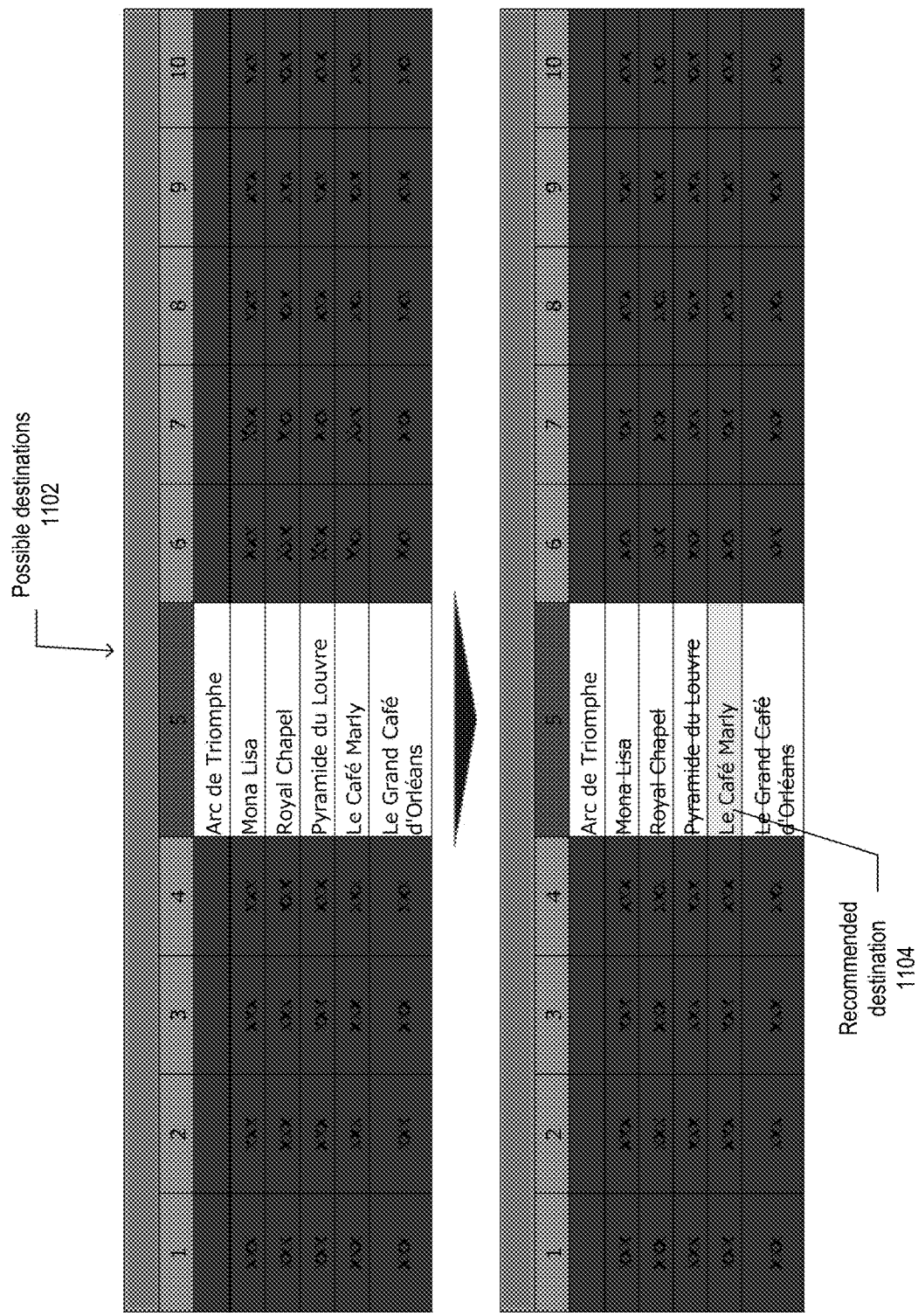
FIG. 11 depicts an example of determining a recommended destination from a recommended cluster according to implementations of the present disclosure.

FIG. 11 depicts an example of determining a recommended destination 1104 from a recommended cluster 1006 according to implementations of the present disclosure. As shown in the example of FIG. 11, the recommended cluster 1006 may include any number of possible destinations 1102. Implementations determine one or more particular recommended destinations 1104 from the possible destinations 1102 based on various criteria. Such criteria may include, but are not limited to: a destination that the user 102 has not already visited on this trip or previous trips; a destination that is within a threshold distance of the user 102, or that is otherwise possible (e.g., convenient) for the user 102 to reach on foot or by transit within a predetermined time period; or a destination that is not excessively divergent from the user's itinerary as indicated by the trip plan information 134.

In some implementations, the statistical correlation between the user 102 and the other users may be omitted, and the recommended cluster 1006 may be identified as the cluster 802 that exhibits the extremum (e.g., maximum) combined emotion metric 902 for the user 102. The recommended destination(s) 1104 may then be selected from the recommended cluster 1006 as described above.

Figure 12A:
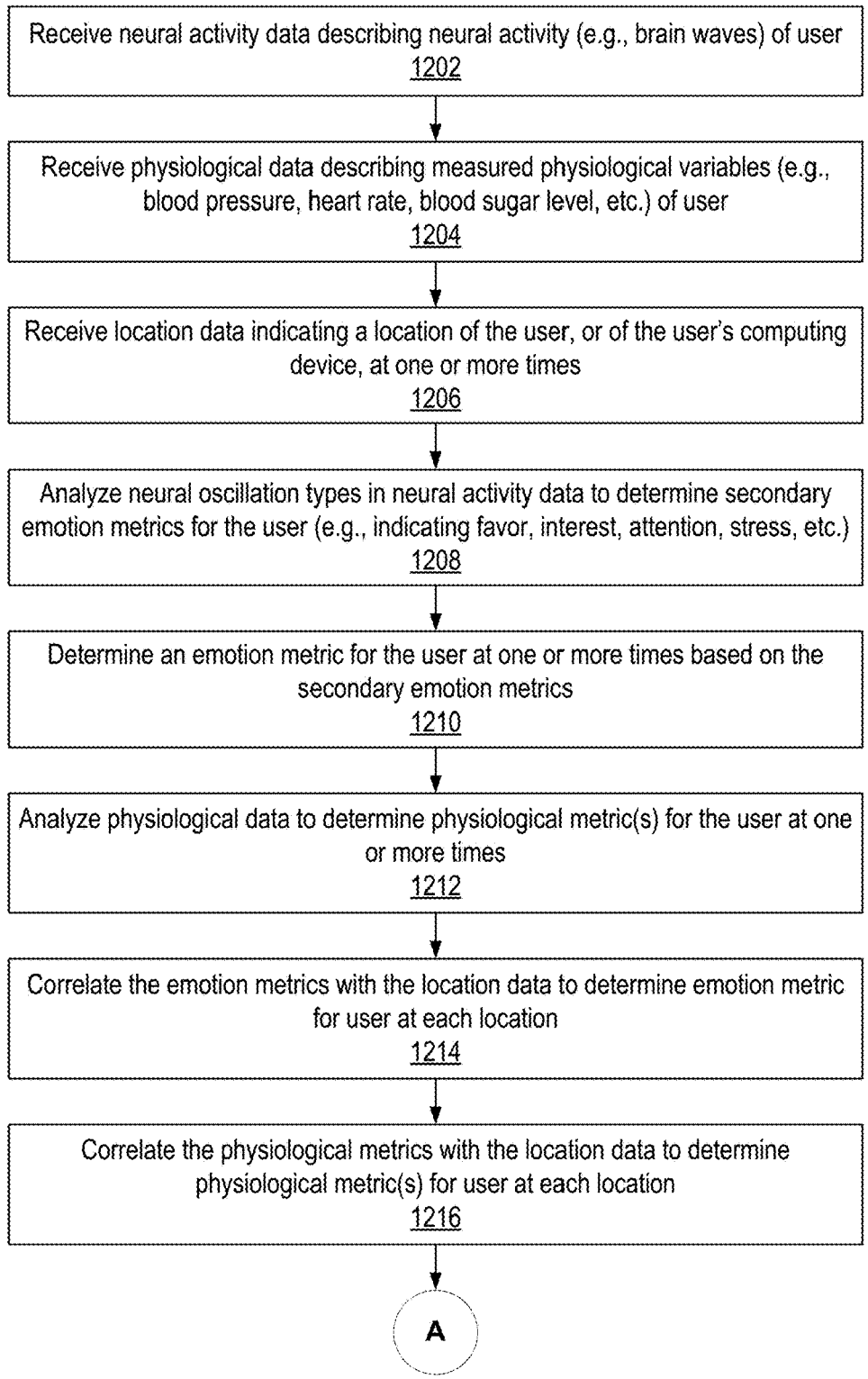
FIGS. 12A-12C depict a flow diagram of an example process for determining recommended destinations for a user according to implementations of the present disclosure.
Figure 12B:
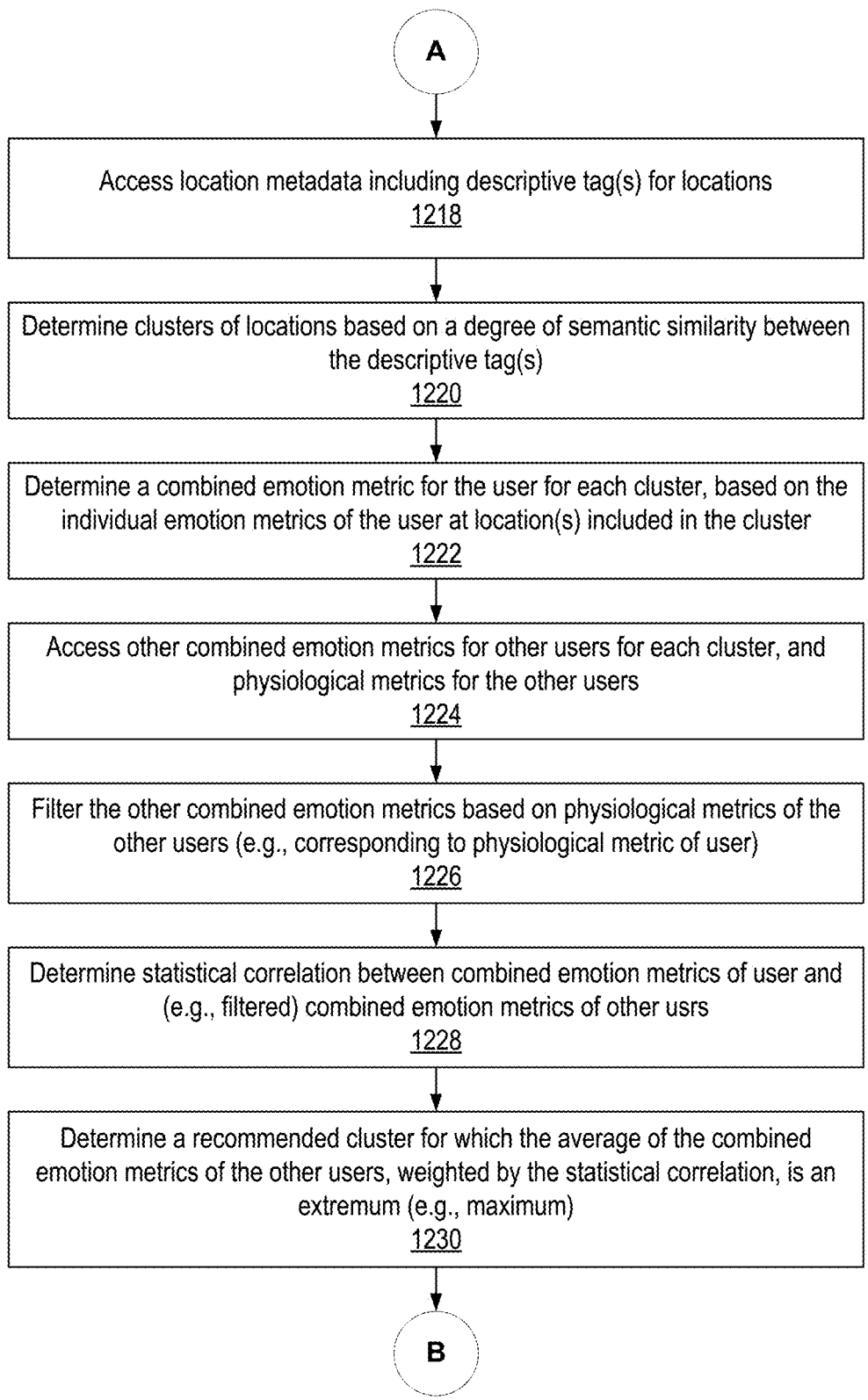
Figure 12C:
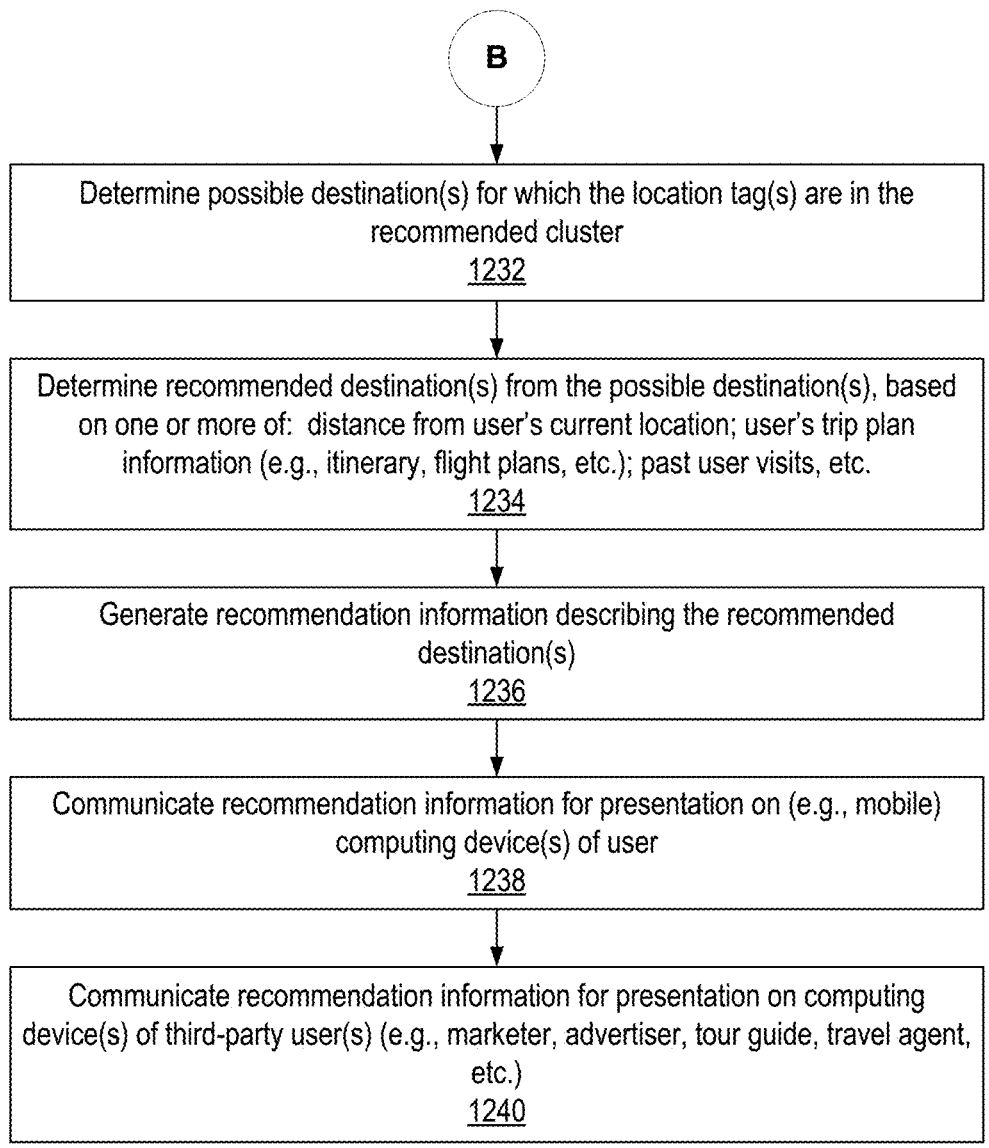

FIGS. 12A-12C depict a flow diagram of an example process for determining recommended destinations for a user 102 according to implementations of the present disclosure. Operations of the process may be performed by one or more of the analysis module(s) 120, the recommendation module(s) 128, or other software module(s) executing on the analysis computing device(s) 118, the mobile device 104, the third-party computing device(s) 136, or elsewhere.

As depicted in FIG. 12A, the neural activity data 110 is received (1202) or otherwise accessed. As described above, the neural activity data 110 may describe neural activity (e.g., brain waves) for a user 102. The physiological data 112 is received (1204) or otherwise accessed. As described above, the physiological data 112 may describe the values of one or more physiological variables for the user 102, such as heart rate, blood pressure, blood sugar level, and so forth. The location data 114 is received (1206) or otherwise accessed. As described above, the location data 114 may describe the location of the mobile device 104 and/or the user 102 at one or more times. As used herein, a time may include a time of day, a date, or both date and time of day. Accordingly, a time may be interpreted as a timestamp indicating a moment in time, or a period of time, to any degree of specificity.

In some implementations, the neural activity data 110 may include multiple neural oscillation types (e.g., brain wave types). The various neural oscillation types may be analyzed (1208) to determine secondary emotion metrics for the user 102. Such secondary emotion metrics may indicate a level of favor, interest, attention, stress, or other emotions experienced by the user 102 at one or more times. In some cases, each of the neural oscillation types may be analyzed to determine a different secondary emotion metric. In some cases, a particular secondary emotion metric may be based on multiple neural oscillation types. The emotion metric 124 for the user 102 at each time may be determined (1210) based on the various secondary emotion metrics.

The physiological data 112 may be analyzed (1212) to determine one or more physiological metrics 126 for the user 102 at one or more times. In some cases, the physiological metric(s) 126 may indicate a level of hunger, fatigue, or other traits of the user 102 at one or more times. In some implementations, the physiological metric(s) 126 may be binary values indicating a presence, or absence, of hunger, fatigue, or other traits in the user 102 at the one or more times.

The emotion metrics 124 may be correlated (1214) with the location data 114 to determine, for the user 102, an emotion metric 124 at one or more of the locations described in the location data 114. Such correlation may be a time-based correlation. For example, the emotion metric 124 at a particular time may be correlated with the location of the user 102 at or near that particular time. The physiological metrics 126 may be similarly correlated (1216) with the location data 114 to determine, for the user 102, a physiological metric 126 at one or more of the locations described in the location data 114. The process is further described with reference to FIG. 12B.

The location metadata 132 may be accessed (1218). As described above, the location metadata 132 may include one or more descriptive tags for each of a plurality of locations. The clusters 802 of locations may be determined (1220) based on a degree of semantic similarity between the descriptive tags for the locations. For example, locations having semantically similar descriptive tags may be designated as being in a particular cluster 802. In some cases, semantic similarity may be determined based on the value of a semantic similarity metric between pairs of locations being less than a predetermined threshold similarity metric. A location may be in a single cluster 802 or in multiple clusters 802.

A combined emotion metric 902 may be determined (1222) for the user 102 for each cluster 802. As described above, the combined emotion metric 902 for a particular cluster 802 may be based on the individual emotion metrics 124 of the user 102 at location(s) included in the cluster 802.

Other combined emotion metrics may be accessed (1224) for each of the clusters 802. In some implementations, the other combined emotion metrics are calculated based on the emotion metrics 124 of other users at various locations. The other combined emotion metrics may have been previously calculated and stored.

In some cases, the other combined emotions metrics are filtered (1226) based on the physiological metrics 126 of the other users. For example, as shown in FIG. 9, the other combined emotion metrics may be filtered to select those for which the physiological metric 126 corresponds to a physiological metric 126 of the user 102. Accordingly, the comparison between the user 102 and the other users may take into account the hunger or fatigue state of the user 102 and the other users.

A statistical correlation 1002 may be calculated or otherwise determined (1228) between the user 102 and each of the other users, as shown in FIG. 10. In some implementations, the statistical correlation 1002 provides a measure of statistical similarity between the combined emotion metrics 902 of the user 102 and the other combined emotion metrics of each of the other users.

A recommended cluster 1006 may be determined (1230) based on the statistical correlations 1002. As described with reference to FIG. 10, a recommendation degree 1004 may be calculated based on the combined emotion metrics 902 of the other users having at least a threshold statistical correlation 1002 with the user 102. In some implementations, the recommendation degree 1004 is an average of the combined emotion metrics 902. The average may be weighted based on the statistical correlations 1002. The cluster 802 having an extremum (e.g., maximum) recommendation value 1004 among the clusters 802 may be designated as a recommended cluster 1006. The process is further described with reference to FIG. 12C.

Possible destination(s) 1102 may be determined (1232) for which the location tag(s) are in the recommended cluster 1006, based on the location metadata 132.

One or more particular recommended destinations 1104 may be determined (1234) from the possible destination(s) 1102. The recommended destination(s) 1104 may be selected based on one or more of the following criteria: the distance from the user's current location to the destination being less than a threshold distance; the location of the destination not diverging excessively from the user's itinerary, based on the trip plan information 134; or the destination not having been previously visited by the user 102, on the current trip or during past trips. Other criteria may also be applied to select the recommended destination(s). In some cases, divergence from an itinerary may be based on a mathematical calculation of distance from a predicted route that the user 102 may follow on a trip, where the route is determined based on itinerary information in the trip plan information 134.

Recommendation information 130 may be generated (1236) describing the recommended destination(s). The recommendation information 130 may be communicated (1238) for presentation of the mobile device 104 or other device(s) operated by the user 102. The recommendation information 130 may also be communicated (1240) for presentation on third-party computing device(s) 136 as described above.

Figure 13:
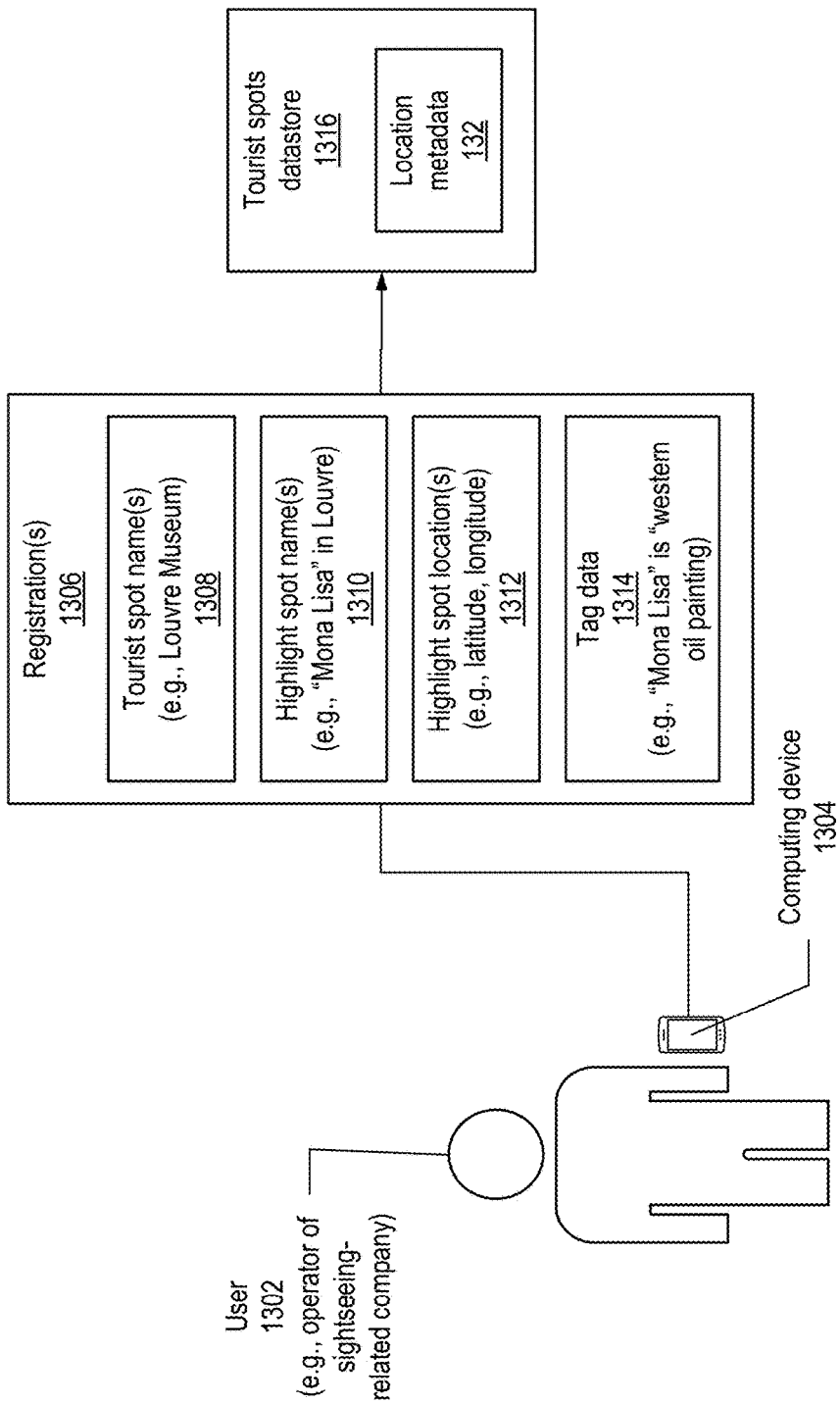
FIG. 13 depicts an example of a process for determining location metadata for one or more locations, according to implementations of the present disclosure.

FIG. 13 depicts an example of a process for determining location metadata 132 for one or more locations. The process for determining location metadata 132 may be described as spot registration of locations. As shown in the example of FIG. 13, a user 1302 may employ a computing device 1304 to specify one or more registrations 1306 which are stored as location metadata 132 in a tourist spot datastore 1316 (e.g., a database or other data storage system). In some cases, the user 1302 is an operator of a sightseeing-related company such as a tour guide business, travel agency, or owner of a store, restaurant, or other business. The user 1302 may also be part of other organizations that provide tourist information, such as a tourist information bureau or other government agency. Although the computing device 1304 is depicted as a smartphone, the computing device 1304 may be any type of computing device (e.g., mobile or otherwise). The registration(s) 1306 may each include: a tourist spot name 1308; one or more highlight spot names 1310 for highlight sites within the tourist spot; highlight spot location(s) 1312 for the highlight spot name(s) 1310, such as latitude/longitude or other coordinates; and tag data 1314, such as descriptive tags for the highlight spots. The registration(s) 1306 may be stored as location metadata 132 in the tourist spots datastore 1316 and used during subsequent analysis to determine recommended destinations as described above.

Figure 14:
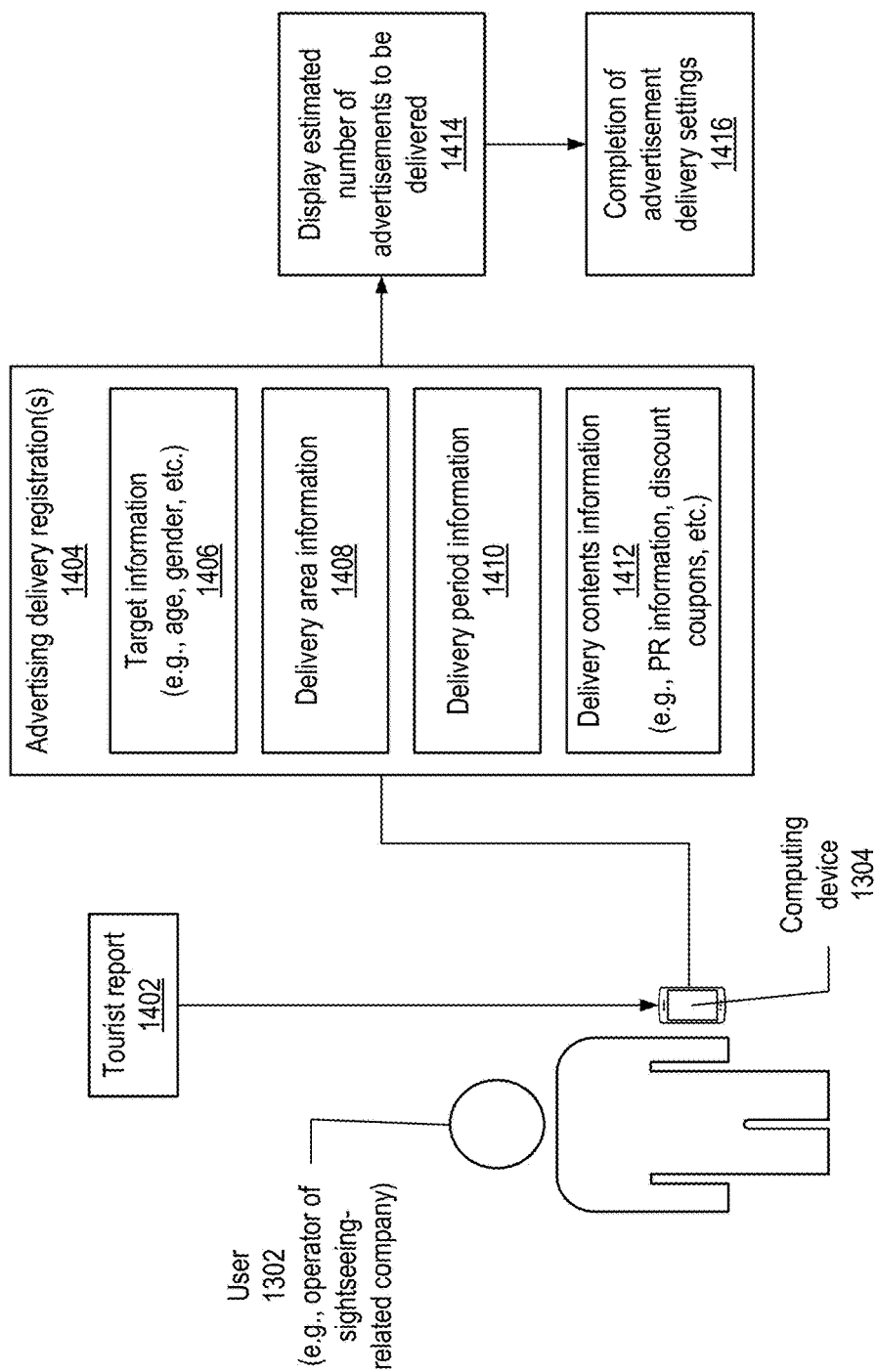
FIG. 14 depicts an example of a process for determining advertisements to deliver to one or more users, according to implementations of the present disclosure.

FIG. 14 depicts an example of a process for determining advertisements to deliver to one or more users. As shown in the example of FIG. 14, the user 1302 (e.g., operator of a sightseeing-related company) may employ the computing device 1304 to receive and view a tourist report 1402. As described above, the tourist report 1402 may indicate, for one or more previous visitors to a location or highlight spot, demographic information regarding the visitors such as age, gender, nationality, language spoken, or other characteristics. The tourist report 1402 may also indicate a degree of excitement of the visitors while visiting the location or spot, as indicated by emotion metrics data.

Based on the tourist report 1402, the user 1302 may employ an application executing on the computing device 1304 to generate one or more advertising delivery registrations 1404. Each advertising delivery registration 1404 may include: target information 1406, such as age, gender, nationality, or other characteristics of the users to be targeted with the advertisement; delivery area information 1408, indicating a radius (e.g., distance or travel time) from the advertised location or site within which users may be presented with the advertisement; delivery period information 1410, indicating how long the advertisement may be presented (e.g., 1 day, 3 days, 1 week, etc.); and delivery contents information 1412, such as public relations information, admission discount coupons, descriptive information, or other information regarding the advertised location or site.

Based on the advertising delivery registration(s) 1404, the application executing on the computing device 1304 may display or otherwise present an estimated number of advertisements to be presented or delivered to users (1414). The user 1302 may then confirm the advertising delivery registration(s) 1404 through the application to complete advertisement delivery settings (1416). The advertisement(s) may be presented as specified in the advertising delivery registration(s) 1404.

Figure 15:
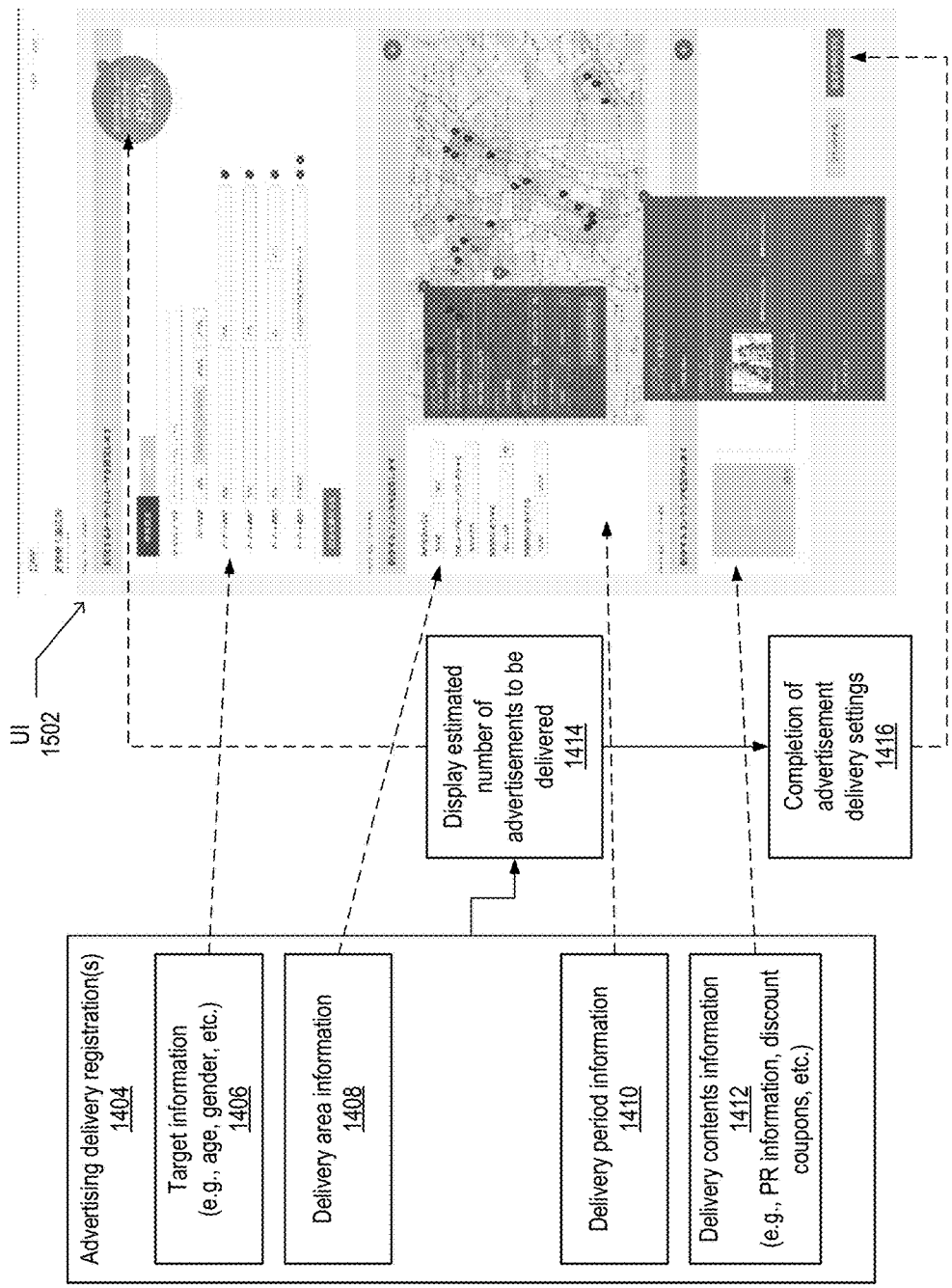
FIG. 15 depicts an example user interface that may be employed in the process for determining advertisements, according to implementations of the present disclosure.

FIG. 15 depicts an example UI 1502 that may be employed in the process for determining advertisements as described with reference to FIG. 14. As shown in the example of FIG. 15, the various data included in the advertising delivery registration(s) 1404 specified by the user 1302 may be presented in one or more portions of the UI 1502. The target information 1406 may be presented in a first portion of the UI 1502, the target information 1406 indicating the selected demographic characteristics of online users to be shown the advertisement(s). The delivery area information 1408 may be presented in a second portion of the UI 1502, the delivery area information 1408 specifying a geographical region in which users may be shown the advertisement(s). The delivery area information 1408 may indicate a region to any degree of specificity, such as a particular building, street, neighborhood, borough, city, county, province, state, prefecture, country, and so forth. In some implementations, the delivery period information 1410 is also presented in the second portion of the UI 1502, the delivery period information 1410 indicating a period of time (e.g., length of advertising campaign) when the advertisement(s) are to be presented. The delivery contents information 1412 may be presented in a third portion of the UI 1502. As shown in the example of FIG. 15, the UI 1502 may also present the estimated number of advertisements to be delivered or the estimated number of users to be exposed to the advertising campaign, based on the information in the advertising delivery registration(s) 1404. The UI 1502 may also include a button or other control that enables the user 1302 to request the completion of advertisement delivery settings 1416. Implementations are not limited to the particular arrangement of information presented in the example UI 1502 of FIG. 15, or to the particular controls, portions, or other UI elements shown in the example of FIG. 15.

Figure 16:
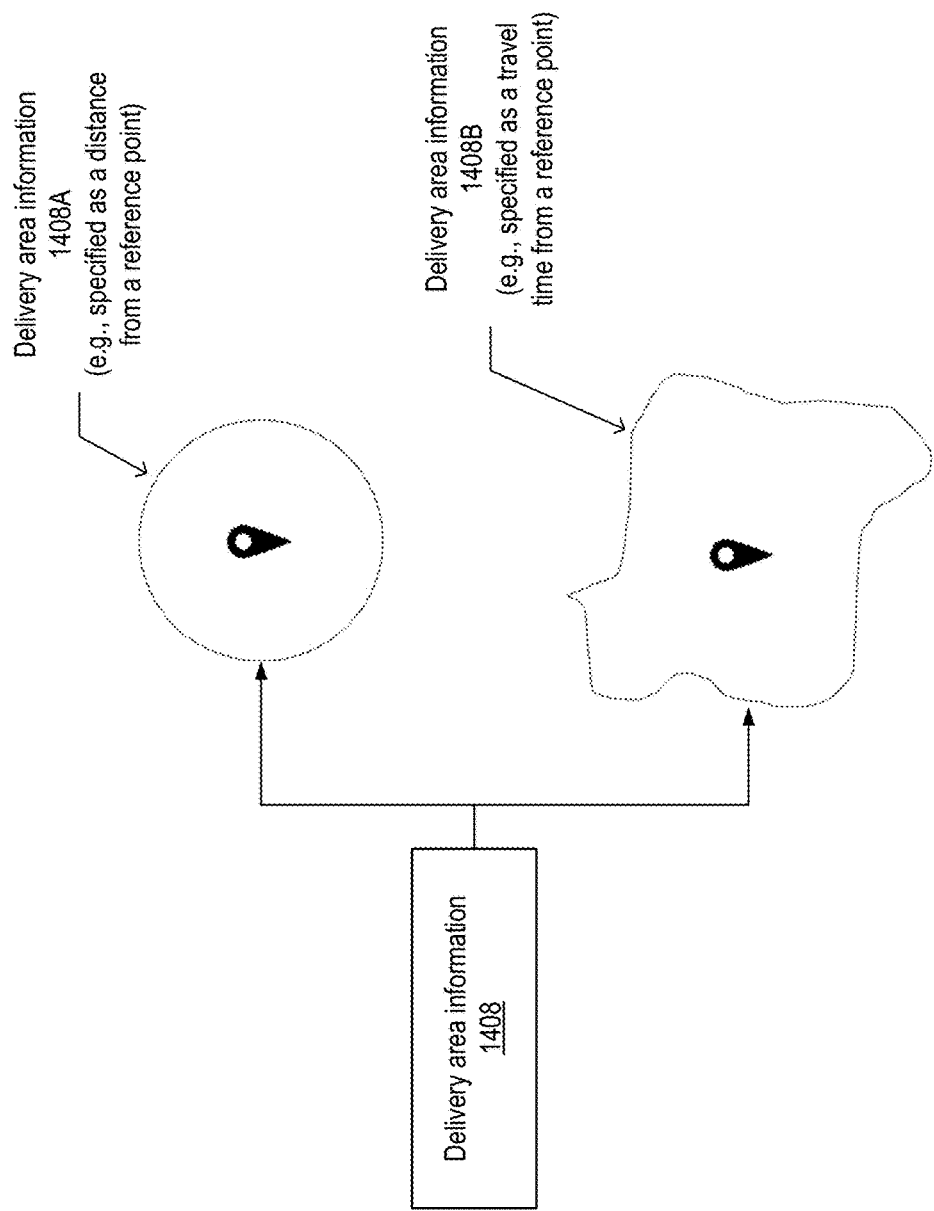
FIG. 16 depicts examples of delivery area information for delivering advertisements or other content, according to implementations of the present disclosure.

FIG. 16 depicts examples of delivery area information 1408 for delivering advertisements or other content. The delivery area information 1408 included in the advertising delivery registration(s) 1404 may be specified as a distance from a reference point or a travel time from a reference point. Implementations also support the specification of delivery area information 1408 using other methods, such as specifying a particular geographical area, postal code, telephone area code, region code, or national code, and so forth. Delivery area information 1408A may be specified as a distance, or radius, from a reference point. For example, the distance may be specified as a range of 500 m, 1 km, 2 km, 3 km, or some other distance from a reference point. Delivery area information 1408B may be specified as a travel time from a reference point, such as 30 minutes, 1 hour, 2 hours, and so forth. The delivery area information 1408B includes the various location(s) that may be reached by an individual travelling from the reference point during the specified travel time. Accordingly, the delivery area information 1408B may be irregularly shaped, and may depend on the various modes of transportation that are available to travel from the reference point, such as walking paths for foot travel, streets for auto travel, bus lines, train lines, subways or other transit systems, and so forth. In some implementations, Mapumental or other tools may be employed to determine the delivery area information 1408B.

FIG. 17 depicts an example of achieving an optimal (e.g., high) CVR for advertising various types of sites, according to implementations of the present disclosure. For example, 5000 tourists may have visited a particular café in the last month. Of those 5000, 1200 may be determined to be excited while visiting the café, or otherwise exhibit positive emotional metric(s), based on neural activity data and/or physiological data. Example distribution 1702 shows a distribution of the 1200 users who exhibited positive emotions at the café. While visiting the café, 1200 users have shown positive emotions, and advertisers may attempt to take advantage of that excitement by presenting the users with advertisements for other nearby sites while the users are still excited by their café experience. The example distribution 1702 shows the distribution of such users who may react positively to different types of sites, such as oil painting, clubs, natural scenery, or shrines.

Based on the delivery area information 1408, e.g., distance-based or travel time-based, or other information in the advertising delivery registration(s) 1404, a determination may be made that advertisements are to be delivered to a maximum of 800 users out of the 1200 who were excited while at the café. Implementations may achieve a high CVR by targeting advertisement delivery to those users best suited, e.g., based on previously measured emotional responses, to react positively to the advertisement(s). Example distribution 1704 shows a distribution of the various types of advertisements that may be presented to the 800 users, determined based on the types of sites that may appeal to each of the 800 users. For each of the 800 users, the type of site that may exhibit a positive emotional response may be determined based on the emotional metrics clustering analysis described above. Although examples herein describe delivering advertisements for presentation on user devices of users, implementations support the delivery and presentation of other types of content such as discount coupons, marketing materials, general tourist information, and so forth.

Figure 18:
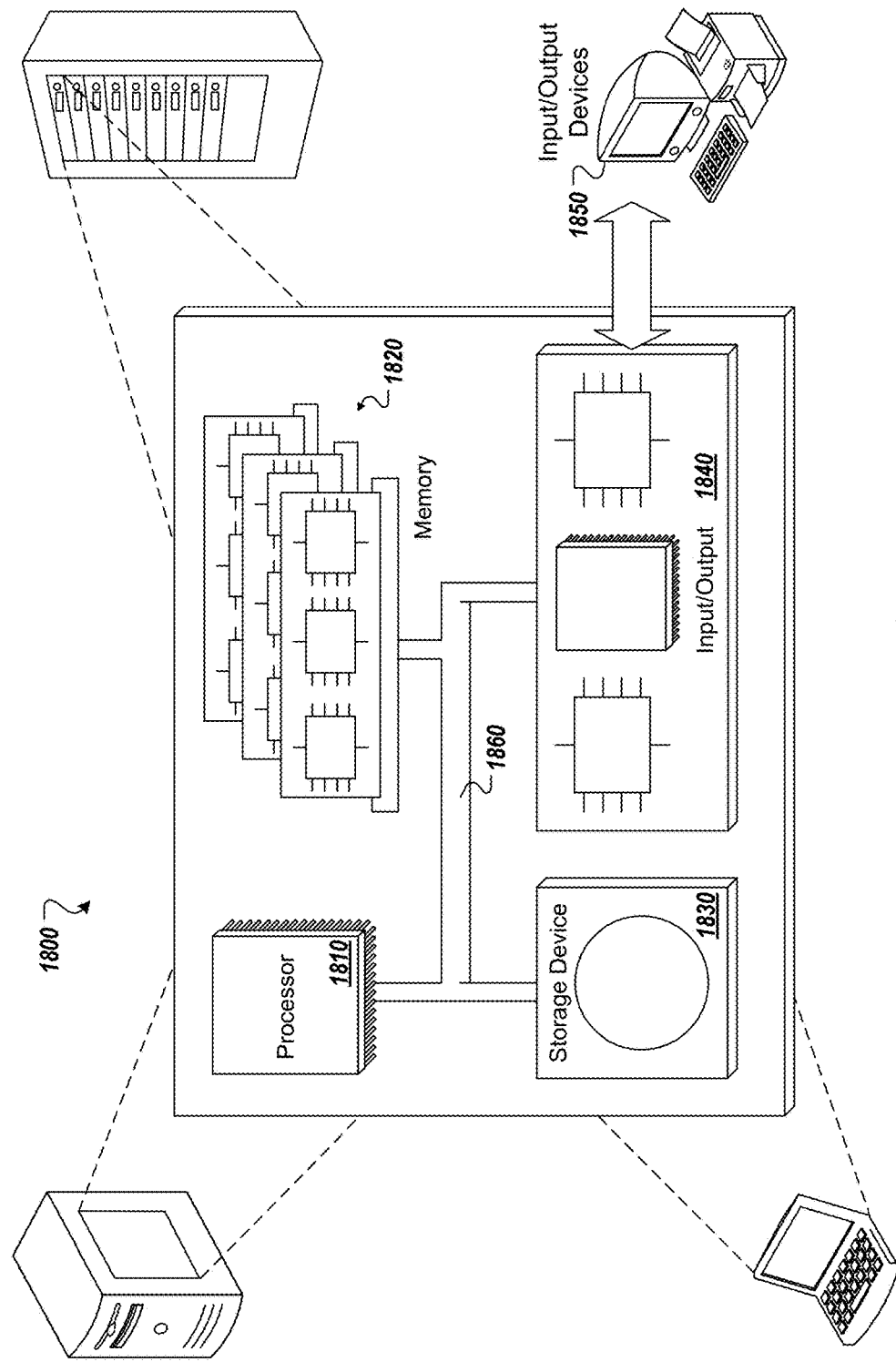
FIG. 18 depicts a schematic diagram of an example computing system, according to implementations of the present disclosure.

FIG. 18 depicts an example computing system 1800 in accordance with implementations of the present disclosure. The system 1800 may be used for any of the operations described with respect to the various implementations discussed herein. For example, the system 1800 may be included, at least in part, in one or more of the analysis computing device(s) 118, the mobile device 104, the third-party computing device 136, or the computing device 1304 described herein. The system 1800 may include one or more processors 1810, a memory 1820, one or more storage devices 1830, and one or more input/output (I/O) devices 1850 controllable via one or more I/O interfaces 1840. Two or more of the components 1810, 1820, 1830, 1840, or 1850 may be interconnected via at least one system bus 1860, which may enable the transfer of data between the various modules and components of the system 1800.

The processor(s) 1810 may be configured to process instructions for execution within the system 1800. The processor(s) 1810 may include single-threaded processor(s), multi-threaded processor(s), or both. The processor(s) 1810 may be configured to process instructions stored in the memory 1820 or on the storage device(s) 1830. The processor(s) 1810 may include hardware-based processor(s) each including one or more cores. The processor(s) 1810 may include general purpose processor(s), special purpose processor(s), or both.

The memory 1820 may store information within the system 1800. In some implementations, the memory 1820 includes one or more computer-readable media. The memory 1820 may include any number of volatile memory units, any number of non-volatile memory units, or both volatile and non-volatile memory units. The memory 1820 may include read-only memory, random access memory, or both. In some cases, the memory 1820 may be employed as active or physical memory by one or more executing software modules.

The storage device(s) 1830 may be configured to provide (e.g., persistent) mass storage for the system 1800. In some implementations, the storage device(s) 1830 may include one or more computer-readable media. For example, the storage device(s) 1830 may include a floppy disk device, a hard disk device, an optical disk device, or a tape device. The storage device(s) 1830 may include read-only memory, random access memory, or both. The storage device(s) 1830 may include one or more of an internal hard drive, an external hard drive, or a removable drive.

One or both of the memory 1820 or the storage device(s) 1830 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 1800. In some implementations, the CRSM may include a data store that provides storage of computer-readable instructions or other information in a non-transitory format. The CRSM may be incorporated into the system 1800 or may be external with respect to the system 1800. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some cases, the processor(s) 1810 and the memory 1820 may be supplemented by, or incorporated into, one or more application-specific integrated circuits (ASICs).

The system 1800 may include one or more I/O devices 1850. The I/O device(s) 1850 may include one or more input devices such as a keyboard, a mouse, a pen, a game controller, a touch input device, an audio input device (e.g., a microphone), a gestural input device, a haptic input device, an image or video capture device (e.g., a camera), or other devices. In some cases, the I/O device(s) 1850 may also include one or more output devices such as a display, LED(s), an audio output device (e.g., a speaker), a printer, a haptic output device, and so forth. The I/O device(s) 1850 may be physically incorporated in one or more computing devices of the system 1800, or may be external with respect to one or more computing devices of the system 1800.

The system 1800 may include one or more I/O interfaces 1840 to enable components or modules of the system 1800 to control, interface with, or otherwise communicate with the I/O device(s) 1850. The I/O interface(s) 1840 may enable information to be transferred in or out of the system 1800, or between components of the system 1800, through serial communication, parallel communication, or other types of communication. For example, the I/O interface(s) 1840 may comply with a version of the RS-232 standard for serial ports, or with a version of the IEEE 1284 standard for parallel ports. As another example, the I/O interface(s) 1840 may be configured to provide a connection over Universal Serial Bus (USB) or Ethernet. In some cases, the I/O interface(s) 1840 may be configured to provide a serial connection that is compliant with a version of the IEEE 1394 standard.

The I/O interface(s) 1840 may also include one or more network interfaces that enable communications between computing devices in the system 1800, or between the system 1800 and other network-connected computing systems. The network interface(s) may include one or more network interface controllers (NICs) or other types of transceiver devices configured to send and receive communications over one or more networks using any network protocol.

Computing devices of the system 1800 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 1800 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some cases, a computing device may include one or more of a virtual computing environment, a hypervisor, an emulation, or a virtual machine executing on one or more physical computing devices. In some cases, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:
1. A system, comprising:
at least one neural activity sensor;
at least one processor; and
a memory communicatively coupled to the at least one processor and storing instructions which, when executed by the at least one processor, cause the at least one processor to perform operations comprising:
receiving neural activity data generated through measurement, by the at least one neural activity sensor, of neural activity of a user at one or more times;
analyzing the neural activity data to determine an emotion metric indicating an emotional state of the user at the one or more times;
correlating the emotion metric at the one or more times with location data indicating one or more locations of the user at the one or more times, the correlating to determine, for the user and for each location, a respective emotion metric that indicates the emotional state of the user while the user is at the respective location;
based on location metadata including descriptive tags for locations, performing semantic clustering to determine clusters of locations based on a degree of semantic similarity between the descriptive tags for the locations;
determining a combined emotion metric for the user and for each of the clusters of locations, based on the respective emotion metrics corresponding to the locations included in the respective cluster;
identifying one of the clusters for which the combined emotion metric is an extremum among the clusters;
determining at least one recommended destination for the user based on each of the at least one recommended destination corresponding to a respective location tag that is in the cluster for which the combined emotion metric is the extremum among the clusters; and communicating recommendation information for presentation on a computing device, the recommendation information describing the at least one recommended destination.

2. The system of claim 1, wherein:

the neural activity data includes a plurality of neural oscillation types exhibited by the user; and analyzing the neural activity data to determine the emotion metric further comprises:

analyzing the plurality of neural oscillation types to determine a plurality of secondary emotion metrics at each of the one or more times; and determining the emotion metric based on the plurality of secondary emotion metrics.

3. The system of claim 2, wherein the plurality of secondary emotion metrics indicate one or more of:

a level of favor of the user;

a level of interest of the user;

a level of attention of the user; or a level of stress of the user.

4. The system of claim 1, wherein determining the at least one recommended destination further comprises:

determining the at least one recommended destination having a location that is within a threshold distance of a current location of the user.

5. The system of claim 1, wherein:

the system further comprises at least one physiological sensor;

the operations further comprise:

receiving physiological data generated through measurement, by the at least one physiological sensor, of one or more physiological variables of the user at the one or more times;

analyzing the physiological data to determine at least one physiological metric of the user at the one or more times; and correlating the at least one physiological metric at one or more times with the location data to determine the at least one physiological metric for the user at each of the one or more locations; and determining the at least one recommended destination for the user is further based, at least in part, on the at least one physiological metric for the user.

6. The system of claim 5, wherein the one or more physiological variables include one or more of:

blood pressure;

heart rate; or blood sugar level.

7. The system of claim 5, wherein the at least one physiological metric includes one or more of:

a hunger level of the user; or a fatigue level of the user.

8. The system of claim 5, wherein determining the at least one recommended destination for the user further comprises:

accessing other combined emotion metrics for each of the clusters, the other combined emotion metrics determined based on emotion metrics for other users exhibiting physiological metrics corresponding to a physiological metric of the user;

determining a statistical correlation between the combined emotion metrics of the user and the other combined emotion metrics of other users;

determining a recommended cluster for which an average of one or more of the other combined emotion metrics of the other users is an extremum; and determining the at least one recommended destination for which a corresponding location tag is in the recommended cluster.

9. The system of claim 8, wherein the average of the one or more of the other combined emotion metrics is weighted based on the statistical correlation.

10. The system of claim 8, the operations further comprising:

determining the one or more of the other combined emotion metrics for which the statistical correlation exceeds a threshold.

11. The system of claim 1, wherein the recommendation information includes at least one advertisement for the at least one recommended destination.

12. A computer-implemented method for determining at least one recommended destination for a user, the method comprising:

analyzing neural activity data to determine an emotion metric indicating an emotional state of the user at one or more times, the neural activity data generated through measurement of neural activity of the user at the one or more times;

correlating the emotion metric at the one or more times with location data indicating one or more locations of the user at the one or more times, the correlating to determine, for the user and for each location, a respective emotion metric that indicates the emotional state of the user while the user is at the respective location;

based on location metadata including descriptive tags for locations, performing semantic clustering to determine clusters of locations based on a degree of semantic similarity between the descriptive tags for the locations;

determining a combined emotion metric for the user and for each of the clusters of locations, based on the respective emotion metrics corresponding to the locations included in the respective cluster;

identifying one of the clusters for which the combined emotion metric is an extremum among the clusters;

determining the at least one recommended destination for the user based on each of the at least one recommended destination corresponding to a respective location tag that is in the cluster for which the combined emotion metric is the extremum among the clusters; and communicating recommendation information for presentation on a computing device, the recommendation information describing the at least one recommended destination.

13. The method of claim 12, wherein:

the neural activity data includes a plurality of neural oscillation types exhibited by the user; and analyzing the neural activity data to determine the emotion metric further comprises:

analyzing the plurality of neural oscillation types to determine a plurality of secondary emotion metrics at each of the one or more times; and determining the emotion metric based on the plurality of secondary emotion metrics.

14. The method of claim 13, wherein the plurality of secondary emotion metrics indicate one or more of:

a level of favor of the user;

a level of interest of the user;

a level of attention of the user; or a level of stress of the user.

15. The method of claim 12, wherein:
the neural activity data is measured by at least one neural activity sensor in proximity to the user.

16. The method of claim 12, wherein determining the at least one recommended destination further comprises:
determining the at least one recommended destination having a location that is within a threshold distance of a current location of the user.

17. The method of claim 12, further comprising:
analyzing physiological data to determine at least one physiological metric of the user at one or more times, the physiological data generated through measurement of one or more physiological variables of the user at the one or more times; and
correlating the at least one physiological metric at one or more times with the location data to determine the at least one physiological metric for the user at each of the one or more locations;
wherein determining the at least one recommended destination for the user is further based, at least in part, on the at least one physiological metric for the user.

18. The method of claim 17, wherein the one or more physiological variables include one or more of:
blood pressure;
heart rate; or
blood sugar level.

19. The method of claim 17, wherein:
the physiological data is measured by at least one physiological sensor in proximity to the user.

20. The method of claim 17, wherein the at least one physiological metric includes one or more of:
a hunger level of the user; or
a fatigue level of the user.

21. The method of claim 17, wherein determining the at least one recommended destination for the user further comprises:
accessing other combined emotion metrics for each of the clusters, the other combined emotion metrics determined based on emotion metrics for other users exhibiting physiological metrics corresponding to a physiological metric of the user;
determining a statistical correlation between the combined emotion metrics of the user and the other combined emotion metrics of other users;
determining a recommended cluster for which an average of one or more of the other combined emotion metrics of the other users is an extremum; and
determining the at least one recommended destination for which a corresponding location tag is in the recommended cluster.

22. The method of claim 21, wherein the average of the one or more of the other combined emotion metrics is weighted based on the statistical correlation.

23. The method of claim 21, further comprising:
determining the one or more of the other combined emotion metrics for which the statistical correlation exceeds a threshold.

24. The method of claim 12, wherein the recommendation information includes at least one advertisement for the at least one recommended destination.

25. One or more non-transitory computer-readable storage media storing instructions which, when executed by at least one processor, cause the at least one processor to perform operations comprising:
analyzing neural activity data to determine an emotion metric indicating an emotional state of the user at one or more times, the neural activity data generated through measurement of neural activity of the user at the one or more times;
correlating the emotion metric at the one or more times with location data indicating one or more locations of the user at the one or more times, the correlating to determine, for the user and for each location, a respective emotion metric that indicates the emotional state of the user while the user is at the respective location;
based on location metadata including descriptive tags for locations, performing semantic clustering to determine clusters of locations based on a degree of semantic similarity between the descriptive tags for the locations;
determining a combined emotion metric for the user and for each of the clusters of locations, based on the respective emotion metrics corresponding to the locations included in the respective cluster;
identifying one of the clusters for which the combined emotion metric is an extremum among the clusters;
determining at least one recommended destination for the user based on each of the at least one recommended destination corresponding to a respective location tag that is in the cluster for which the combined emotion metric is the extremum among the clusters; and
communicating recommendation information for presentation on a computing device, the recommendation information describing the at least one recommended destination.

26. The one or more non-transitory computer-readable storage media of claim 25, wherein:
the neural activity data includes a plurality of neural oscillation types exhibited by the user; and
analyzing the neural activity data to determine the emotion metric further comprises:
analyzing the plurality of neural oscillation types to determine a plurality of secondary emotion metrics at each of the one or more times; and
determining the emotion metric based on the plurality of secondary emotion metrics.

27. The one or more non-transitory computer-readable storage media of claim 26, wherein the plurality of secondary emotion metrics indicate one or more of:
a level of favor of the user;
a level of interest of the user;
a level of attention of the user; or
a level of stress of the user.

28. The one or more non-transitory computer-readable storage media of claim 25, wherein:
the neural activity data is measured by at least one neural activity sensor in proximity to the user.

29. The one or more non-transitory computer-readable storage media of claim 25, wherein determining the at least one recommended destination further comprises:
determining the at least one recommended destination having a location that is within a threshold distance of a current location of the user.

30. The one or more non-transitory computer-readable storage media of claim 25, the operations further comprising:
analyzing physiological data to determine at least one physiological metric of the user at one or more times, the physiological data generated through measurement of one or more physiological variables of the user at the one or more times; and correlating the at least one physiological metric at one or more times with the location data to determine the at least one physiological metric for the user at each of the one or more locations;

wherein determining the at least one recommended destination for the user is further based, at least in part, on the at least one physiological metric for the user.

31. The one or more non-transitory computer-readable storage media of claim 30, wherein the one or more physiological variables include one or more of:
blood pressure;
heart rate; or
blood sugar level.

32. The one or more non-transitory computer-readable storage media of claim 30, wherein:
the physiological data is measured by at least one physiological sensor in proximity to the user.

33. The one or more non-transitory computer-readable storage media of claim 30, wherein the at least one physiological metric includes one or more of:
a hunger level of the user; or
a fatigue level of the user.

34. The one or more non-transitory computer-readable storage media of claim 30, wherein determining the at least one recommended destination for the user further comprises:
accessing other combined emotion metrics for each of the clusters, the other combined emotion metrics determined based on emotion metrics for other users exhibiting physiological metrics corresponding to a physiological metric of the user;
determining a statistical correlation between the combined emotion metrics of the user and the other combined emotion metrics of other users;
determining a recommended cluster for which an average of one or more of the other combined emotion metrics of the other users is an extremum; and
determining the at least one recommended destination for which a corresponding location tag is in the recommended cluster.

35. The one or more non-transitory computer-readable storage media of claim 34, wherein the average of the one or more of the other combined emotion metrics is weighted based on the statistical correlation.

36. The one or more non-transitory computer-readable storage media of claim 34, further comprising:
determining the one or more of the other combined emotion metrics for which the statistical correlation exceeds a threshold.

37. The one or more non-transitory computer-readable storage media of claim 25, wherein the recommendation information includes at least one advertisement for the at least one recommended destination.

* * * * *